US009452190B2

(12) United States Patent
Samach et al.

(10) Patent No.: US 9,452,190 B2
(45) Date of Patent: Sep. 27, 2016

(54) NEUROPROTECTIVE NATURAL EXTRACT FROM PASSION FRUIT

(71) Applicants: Yissum Research Development Company of the Hebrew University of Jerusalem Ltd., Jerusalem (IL); The State of Israel, Ministry of Agriculture & Rural Development, Agricultural Research Organization (ARO) (Volcani Center), Beit-Dagan (IL)

(72) Inventors: Alon Samach, Rehovot (IL); Oren Tirosh, Nes Ziona (IL); Edna Pesis, Nes Ziona (IL); Avital Artan, Rehovot (IL); Livnat Goldenberg, Rehovot (IL); Aron Troen, Mazkeret Batya (IL)

(73) Assignees: THE STATE OF ISRAEL, MINISTRY OF AGRICULTURE & RURAL DEVELOPMENT, AGRICULTURAL RESEARCH ORGANISATION (ARO) (VOLCANI CENTER), Beit-Dagan (IL); YISSUM RESEARCH DEVELOPMENT COMPANY OF THE HEBREW UNIVERSITY OF JERUSALEM LTD., Givat Ram, Jerusalem (IL)

( * ) Notice: Subject to any disclaimer, the term of this patent is extended or adjusted under 35 U.S.C. 154(b) by 0 days.

(21) Appl. No.: 14/597,674

(22) Filed: Jan. 15, 2015

(65) Prior Publication Data

US 2015/0182569 A1 Jul. 2, 2015

Related U.S. Application Data

(63) Continuation of application No. 13/807,024, filed as application No. PCT/IL2011/000515 on Jun. 28, 2011, now abandoned.

(60) Provisional application No. 61/359,073, filed on Jun. 28, 2010.

(51) Int. Cl.
| | |
|---|---|
| *A61K 36/00* | (2006.01) |
| *A61K 36/185* | (2006.01) |
| *A23L 1/222* | (2006.01) |
| *A23L 1/30* | (2006.01) |

(52) U.S. Cl.
CPC ............ *A61K 36/185* (2013.01); *A23L 1/2225* (2013.01); *A23L 1/3002* (2013.01); *A23V 2002/00* (2013.01)

(58) Field of Classification Search
None
See application file for complete search history.

(56) References Cited

U.S. PATENT DOCUMENTS

2003/0133965 A1* 7/2003 Bruno .................. A23L 1/3004
424/439

FOREIGN PATENT DOCUMENTS

| EP | 1854470 | 11/2007 |
|---|---|---|
| JP | 07126179 A * | 5/1995 |
| JP | 07126179 A1 | 5/1995 |
| JP | 2009102298 A * | 5/2009 |
| WO | 2005/09715 | 10/2005 |

OTHER PUBLICATIONS

Aderinwale et al, Current therapies and new strategies for the management of Alzheimers disease. American Journal of Alzheimer's Disease and other Dementias, (Aug. 2010) vol. 25, No. 5, pp. 414-424.*
Ryan et al, Correlating familial Alzheimers disease gene mutations with clinical phenotype. Biomarkers in Medicine, (Feb. 2010) vol. 4, No. 1, pp. 99-112.*
Zhang, Loss of function of ATXN1 increases amyloid beta-protein levels by potentiating beta-secretase processing of beta-amyloid precursor protein. The Journal of biological chemistry, (Mar. 19, 2010) vol. 285, No. 12, pp. 8515-8526.*
Corvol teaches Neuroprevention: A new challenge? Revue Neurologique, (Nov. 2012) vol. 168, No. 11, pp. 796-801.*
Davis, Comparative study of inhibition at multiple stages of amyloid-beta self-assembly provides mechanistic insight. Molecular pharmacology, (Aug. 2009) vol. 76, No. 2, pp. 405-413. Electronic Publication Date: May 29, 2009.*
Bacskai, Four-dimensional multiphoton imaging of brain entry, amyloid binding, and clearance of an amyloid-beta ligand in transgenic mice. Proceedings of the National Academy of Sciences of the United States of America, (Oct. 14, 2003.*
Schenk, Immunotherapy with beta-amyloid for Alzheimer's disease: a new frontier. DNA and cell biology, (Nov. 2001) vol. 20, No. 11, pp. 679-681.*
Nechiporuk, Linkage of familial Alzheimer disease to chromosome 14 in two large early-onset pedigrees: effects of marker allele frequencies on lod scores. American journal of medical genetics, (May 1, 1993) vol. 48, No. 1, pp. 63-66.*
Sena, Neuropharmacological activity of the pericarp of Passiflora edulis flavicarpa degener: putative involvement of C-glycosylflavonoids. Experimental biology and medicine (Maywood, N.J.), (Aug. 2009) vol. 234, No. 8, pp. 967-975. Electronic Publication Date: Jun. 2, 2009.*

(Continued)

*Primary Examiner* — Qiuwen Mi
(74) *Attorney, Agent, or Firm* — Browdy and Neimark, PLLC

(57) ABSTRACT

Methods for the treatment and prevention of neural cell and neuro-pathological disorders are provided, comprising contacting the neural cells, or administering to a subject in need thereof, botanical raw material (BRM) or an extract obtainable from passion fruits. Compositions, as well as a nutraceutical composition comprising the same are also provided.

8 Claims, 14 Drawing Sheets

(56) References Cited

OTHER PUBLICATIONS

Federico, New C-deoxyhexosyl flavones and antioxidant properties of Passiflora edulis leaf extract. Journal of agricultural and food chemistry, (Dec. 12, 2007) vol. 55, No. 25, pp. 10187-10193. Electronic Publication Date: Nov. 15, 2007.*
Zhu et al, Reactive Oxygen Species: Stuck in the Middle of Neurodegeneration. Journal of Alzheimer's Disease (2010), 20(Suppl. 2), S357-S367.*
Aharoni-Simon et al. (2006) "*ROS-Production-Mediated Activation of AP-1 but Not NFκB Inhibits Glutamate-Induced HT4 Neuronal Cell Death*," Antioxidants Redxo Signaling, 8:1339-1349.
Akhondzadeh et al. (2001) "*Passionflower in the treatment of generalized anxiety: a pilot double-blind randomized controlled trial with oxazepam*," J. Clin. Pharma. Thera, 26:363-367.
Budick-Harmelin N. et al. (2008) "*Triglycerides Potentiate the Inflammatory Response in Rat Kupffer Cells*," Antioxid. Redox. Signal., 10:2009-2022.
Campeol, E. et al. (2001) "*Volatile Compounds from Three Cultivars of Olea europaea from Italy*," J. Agri. Food Chem., 49:5409-5411.
Chan H.T. et al. (1972) "*Nonvolatile Acids of Passion Fruit Juice*," J. Agric. Food Chem., 20:110-112.
Coyle, J.T. and Puttfarcken, P. (1993) "*Oxidative Stress, Glutamate, and Neurodegenerative Disorders*," Science, 262:689-695.
De Oliveira et al. (2009) "*Total phenolic content and free radical scavenging activities of methanolic extract powders of tropical fruit residues*," Food Chemistry 115(2):469-475.
Demyttenaere, J.C.R. et al. (2003) "*Flavour analysis of Greek white wine by solidphase microextrraction-capillary gas chromatography-mass spectrometry*," J. Chromatogr. A 985:233-246.
Engel, K. and Tressl, R. (1991) "*Identification of New Sulfur-containing Volatiles in Yellow Passion Fruits (Passiflora edulis f. flavicarpa)*," J. Agric. Food Chem. 39:2249-2252.
Joseph et al (1998) "*Long-Term Dietary Strawberry, Spinach, or Vitamen E Supplementation Retards the Onset of Age-Related Neuronal Signal-Transduction and Cognitive Behavioral Deficits*," J. Neurosci., 18:8047-8055.
Murphy, T.H., et al. (1989) "*Glutamate Toxicity in a Neuronal Cell Line Involves Inhibition of Cystine Transport Leading to Oxidative Stress*," Neuron 2(6):1547-1558.
Murray, K., et al. (1972) "*The Chemistry of Food Flavour*," Aust. J. of Chem. 25: 1921-1933.
Pesis E. et al., (2000) "*Modified atmosphere and modified humidity packaging alleviates chilling injury symptoms in mango fruit*," Postharvest Biol. and Technol. 19:93-101.
Pino, J.A.; et al., (2002) "*Volatile Compounds of Psidium slautare (H.B.K.) Berg. Fruit*," J. Agri. Food Chem., 50:5146-5148.
Pontes, M. et al. (2009) "*Headspace solid-phase microextraction-gas chromatography-quadrupole mass spectrometric methodology for the establishment of the volatile composition of Passiflora fruit species*," Microchemical J., 93(1):1-11.
Prestwich, G.D., et al. (1976) "*Synthesis and Structures of Diheydroedulan I and II Trace Components from the Juice of Passiflora Edulis Sims*," Tetrahedron 32:2945-2948.
Pruthi J.S. and Lal G (1958) "*Carotenoids in Passion Fruit Juice*," J. Food Sci. 23:505-510.
Savolainen, K.M., et al. (1998) "*Interactions of excitatory neurotransmitters and xenobiotics in excitotoxicity and oxidative stress: glutamate and lead*," Toxicol. Left. 102-103:363-367.
Scafato, P., et al. (2009) "*A New Efficient Enantioselective Synthesis of (+)-cis-2- Methyl-4-Propyl-1, 3-Oxathiane, a Valuable Ingredient for the Aroma of Passion Fruit*," Chirality 21:176-182.
Sen, C.K., et al. (2000) "*Tocotrienol Potently Inhibits Gludtamate-Induced pp60$^{cSrc}$ Kinase Activation and Death of HT4 Neuronal Cells*," J. Biol. Chem. 275(17):13049-13055.
Shukitt-Hale B et al. (1998) "*Pyschomotor and Spatial Memory Performance in Aging Male Fischer 344 Rats*," Exp. Gerontol. 33:615-624.

Swiegers, J., et al. (2007) "*Engineering volatile thiol release in Saccharomyces cerevisiae for improved wine aroma*," Yeast 24:561-574.
Talcott S.T. et al., (2003) "*Phtochemical Composition and Antioxidant Stability of Fortified Yellow Passion Fruit (Passiflora edulis)*," J. Agric. Food Chem. 51:935-941.
Tan, S., et al. (2001) "*Oxytosis: A Novel Form of Programmed Cell Death*," Curr. Top. Med. Chem. 1(6):497-506.
Tapp E.J. et al. (2008) "*Determination and Isolation of a Thioesterase from Passion fruit (Passiflora edulis Sims) That Hydrolyzes Volatile Thioesters*," J. Agric. Food Chem. 56:6623-6630.
Tietel, Z. et al. (2010) "*Effects of wax coatings and postharvest storage on sensory quality and aroma volatile composition of 'Mor' mandarins*," J. Sci. Food Agric. 90(6):995-1007.
Tirosh O. et al. (2003) "*Mitochondrion-mediated apoptosis is enhanced in long-lived aMUPA transgenic mice and calorically restricted wild-type mice*," Exp. Gerontol. 38:955-963.
Tominaga, T. and Dubourdieu, D. (2000) "*Identification of Cysteinylated Aroma Precursors of Certain Volatile Thiols in Passion Fruit Juice*," J. Agric. Food. Chem. 48:2874-2876.
Troen A.M. et al. (2008) "*Cognitive Impairment in Folate-Deficient Rats Corresponds to Depleted Brain Phosphatidylcholine and Is Prevented by Dietary Methionine without Lowering Plasma Homocysteine*," J. Nutr. 138:2502-2509.
Werkhoff, P., et al. (1998) "*Vacuum Headspace Method in Aroma Research: Flavor Chemistry of Yellow Passion Fruits*," J. Agric. Food Chem. 46:1076-1093.
ISR PCT/IL2011/000515 (Date of mailing: Jan. 17, 2012).
Aderinwale et. al. (Aug. 2010) "*Current therapies and new strategies for the management of Alzheimer's disease*, Am. J. Alzheimer's Disease and other Dementias," 25(5):414-424.
NIH State-of-the-Science Conference, "Preventing Alzheimer's Disease and Cognitive Decline," Program and Abstracts (Apr. 26-28, 2010).
Ryan et al. (2010) "*Correlating familial Alzheimer's disease gene mutations with clinical phenotype*," Biomarkers in Medicine 4(1):99-112.
Zhang et al. (2010) "*Loss of function of ATXN1 increases amyloid beta-protein levels by potentiating beta-secretase processing of beta-amyloid precursor protein*," J. Biological Chemistry 285(12):8515-8526.
Selkoe, Dennis J. (2012) "*Preventing Alzheimer's Disease*," Science 337:1488-1492.
Corvol (2012) "*Neuroprevention: A new challenge?*" Revue Neurologique 168(11):796-801.
Davis et al. (2009) "*Comparative study of inhibition at multiple stages of amyloid-beta self-assembly provides mechanistic insight*," Molecular Phara. 76(2):405-413.
FDA Regulation of Genetic Tests, Genetics & Public Policy Center publication, updated May 30, 2008.
Bacskai et al. (2003) "*Four-dimensional multiphotom imaging of brain entry, amyloid binding, and clearance of an amyloid-beta ligand in transgenic mice*," Pr. Natl. Acad. Sci. 100(21):12462-7.
Schenk et al. (2001) "*Immunotherapy with beta-amyloid for Alzheimer's disease: a new frontier*," DNA and Cell Biol. 20(11):679-81.
Nechiporuk et al. (1993) "Linkage of familial Alzheimer disease to chromosome 14 in two large early-onset pedigrees: effects of marker allele frequencies on lod scores," Amer. J. Med. Genetics 48(1):63-6.
Sena et al. (2009) "*Neuropharmacological Activity of the Pericarp of Passiflora edulis flavicarpa Degener: Putative Involvement of C-Glycosylfavonoids*," Exp Biol Med 234(8):967-975.
*Diagnostic and Statistical Manual of Mental Disorders*, 4$^{th}$ Edition, Text Revision (DSM-IV-TR: TR Version 2000) (selected abstracts).
Ferreres et al. (2007) "*New C-Deoxyhexosyl Flavones and Antioxidant Properties of Passiflora edulis Leaf Extract*," J. Agric. Food Chem. 55:10187-10193.
Patten et al. (2010) "*Reactive Oxygen Species: Stuck in the Middle of Neurodegeneration*," J. Alzheimer's Disease 20(2):S357-S367.
Plaumann et al. (1996) "*Flavonoids activate wild-type p. 53*," Oncogene 13:1605-1614.

(56) References Cited

OTHER PUBLICATIONS

Wang et al. (1999) "*Induction of Apoptosis by Apigenin and Related Flavonoids Through Cytochrome c Release and Activation of Caspase-9 and Caspase-3 in Leukemia HL-60 Cells*," European J. Cancer 35(10):1517-1525.

Ferguson et al. (2004) "*A Flavonoid Fraction from Cranberry Extract Inhibits Proliferation of Human Tumor Cell Lines*," J. Nutrition 1529-1535.

Bittigau et al. (2002) "*Antiepileptic drugs and apoptotic neurodegeneration in the developing brain*," PNAS 99(23):15089-94.

Seelinger et al. (2008) "*Anti-carcinogenic Effects of the Flavonoid Luteolin*," Molecules 13:2628-2651.

Dean, Elizabeth (2008) "*Apoptosis in Neurodegeneration: Programmed Cell Death and its Role in Alzheimer's and Huntington's Diseases*," Eukaryon, vol. 4, Lake Forest College 4:42-47.

Friedlander, Robert M. (2003) "*Apoptosis and Caspases in Neurodegenerative Diseases*," The New England Journal of Medicine 348(14):1365-1375).

Jue et al. (2007) "*A Critical Role of Luteolin-Induced Reactive Oxygen Species in Blockage of Tumor Necrosis Factor-Activated Nuclear Factor-κB Pathway and Sensitization of Apoptosis in Lung Cancer Cells*," Mol. Pharmacology 71(5):1381-1388.

Goldenberg et al., "Ripening attributes of new passion fruit line featuring seasonal nonclimacteric behavior" J Agric Food Chem. 60(7):1810-21 (2012) (Abstract).

\* cited by examiner

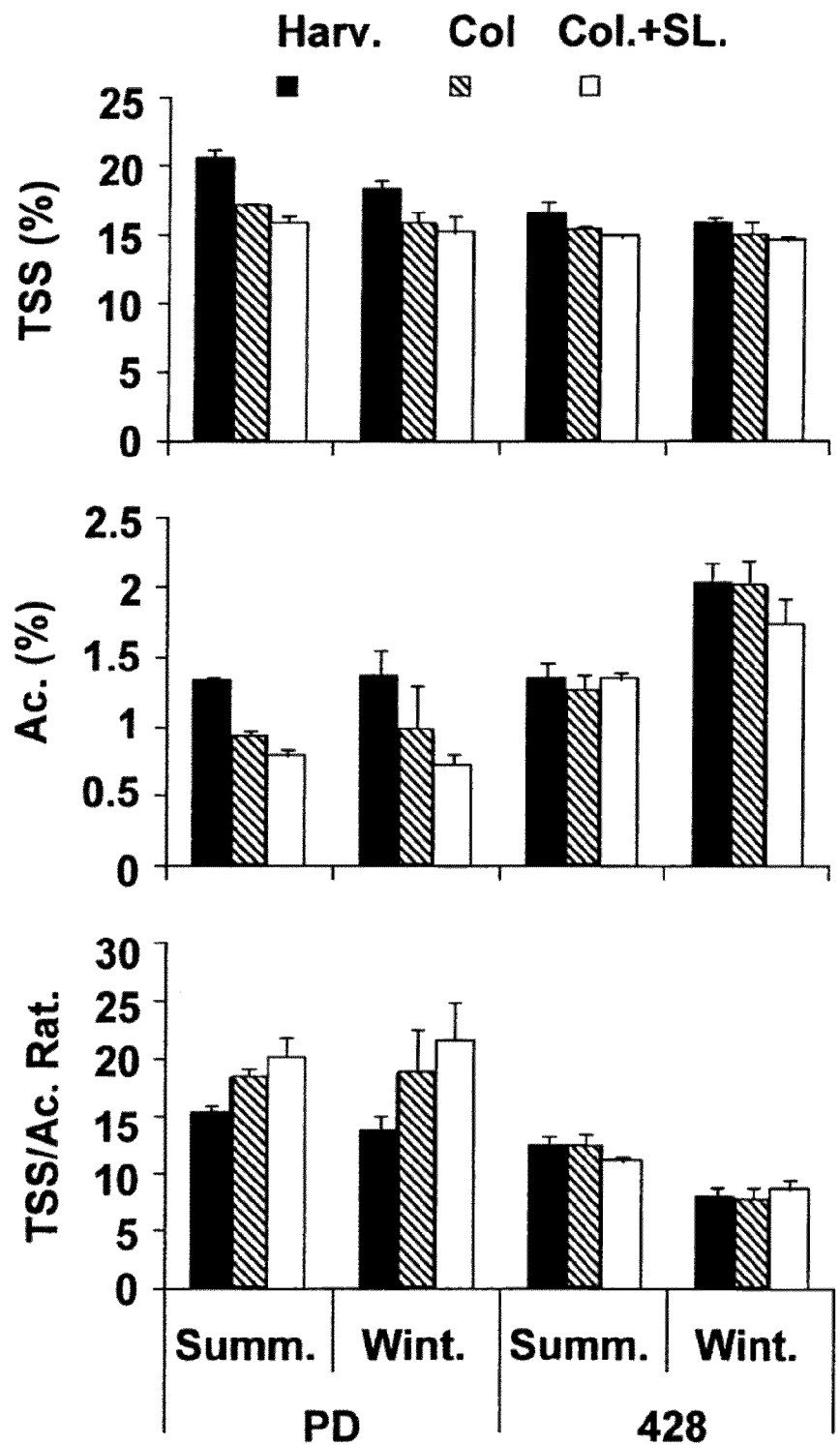

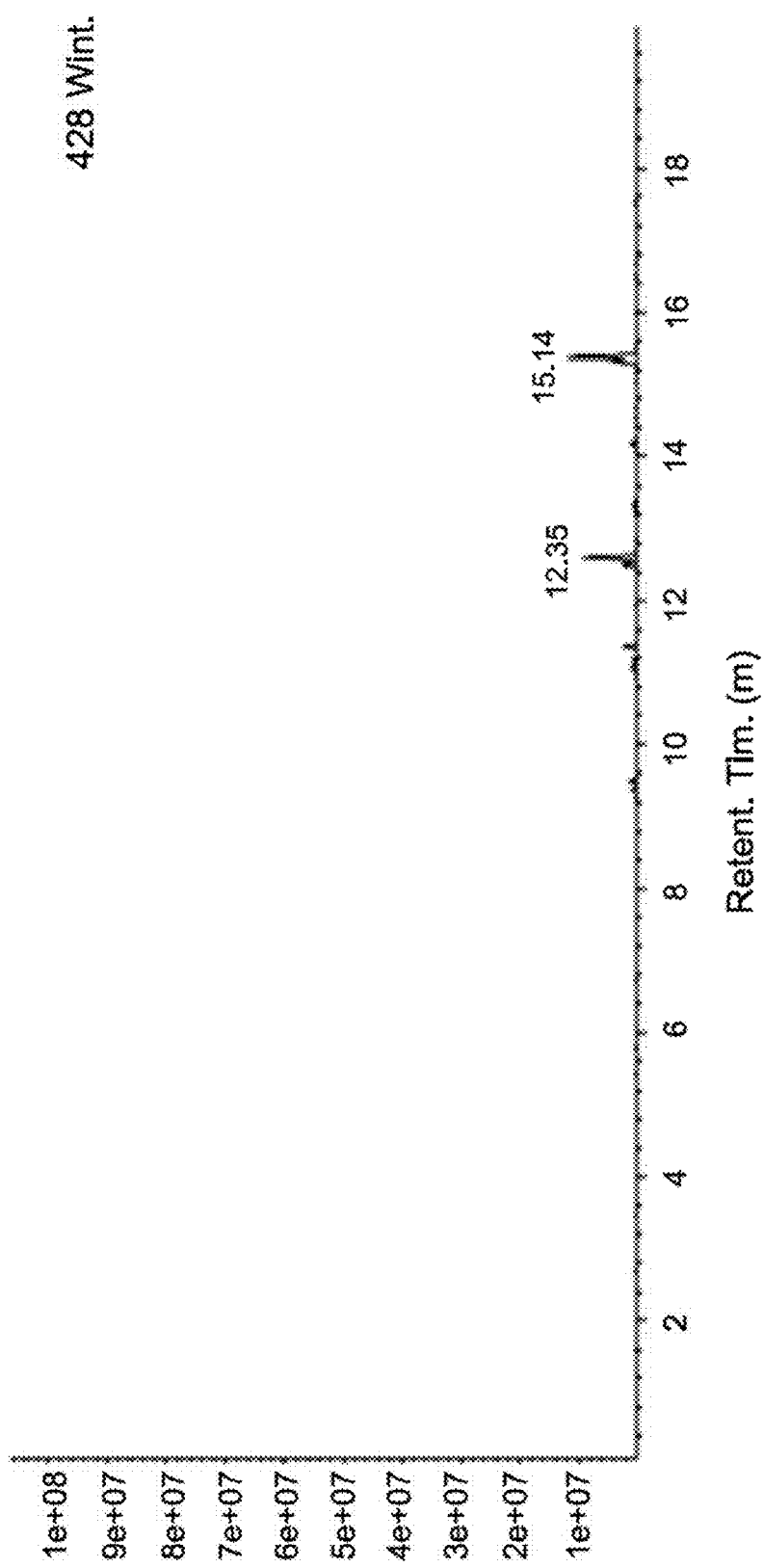

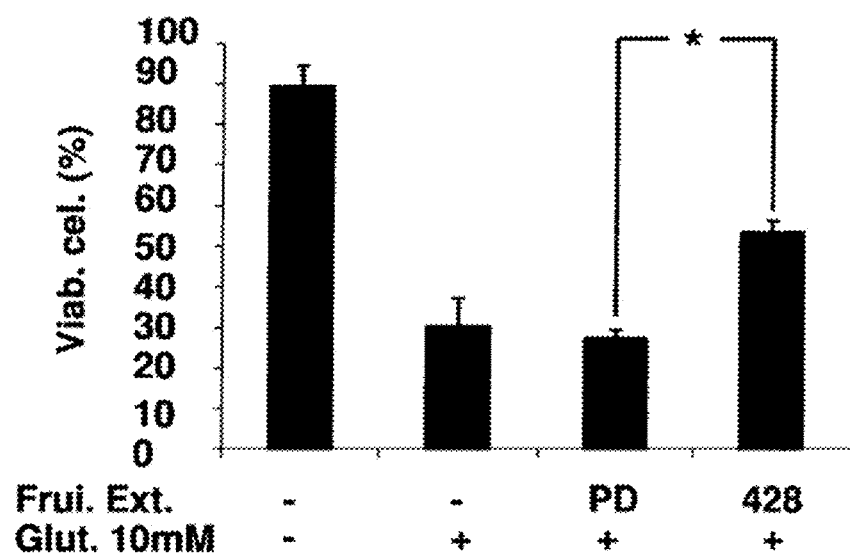
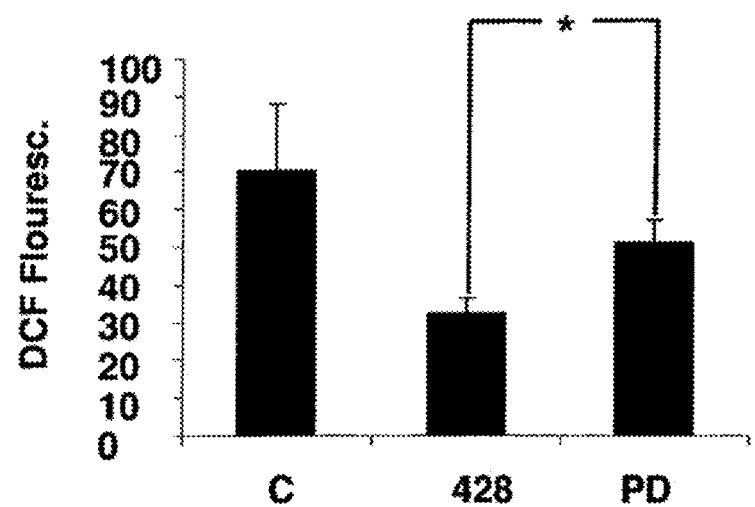

NEUROPROTECTIVE NATURAL EXTRACT FROM PASSION FRUIT

CROSS-REFERENCE TO RELATED APPLICATIONS AND CLAIM TO PRIORITY

This application is a continuation of U.S. application Ser. No. 13/807,024 (filed Mar. 9, 2013), which application is a §371 National Stage Application of PCT/IL2011/000515 (filed Jun. 28, 2011), which application claims priority to U.S. Patent Application Ser. No. 61/359,073 (filed Jun. 28, 2010), each of which applications is incorporated herein by reference in its entirety and to which priority is claimed.

FIELD OF THE INVENTION

The invention relates to natural neuroprotective extracts and preparations and uses thereof in treating neuro-pathological conditions. More specifically, the invention provides neuroprotective passion fruit extracts, compositions and botanical drugs thereof, for use in treatment of neuro-pathological disorders.

BACKGROUND OF THE INVENTION

All publications mentioned throughout this application are fully incorporated herein by reference, including all references cited therein.

The degeneration and/or death of cells in the nervous system are a major factor in many diseases and medical conditions. Such diseases and conditions include traumatic brain injuries, traumatic spinal cord injuries, stroke, hypoxia or ischemia related to decreased neural perfusion, secondary to cardiac arterial bypass graft surgery (CABG), neurodegenerative disorders such as Parkinson's disease, Alzheimer's disease, multiple sclerosis, amyotrophic lateral sclerosis (ALS) and other neurodegenerative diseases as well as decrease in neuronal function associated with normal aging processes. It is of interest to prevent or decrease such cell death and degeneration and to minimize the loss of neural function.

Nutritional status is an important determinant of risk for neurodegenerative disease and cognitive decline among old adults. Deficiencies of nutrients including omega-3 fatty acids, B-vitamins, and antioxidants can exacerbate or increase susceptibility to pathological processes such as glutamate-induced neuronal injury that is a prominent feature of Alzheimer's and Parkinson's disease, epilepsy and stroke. Theoretically, nutrients and natural compounds found in edible fruits can mitigate some of this damage and can therefore play an important role in a comprehensive approach to neuro-protection. However, actionable evidence for the neuroprotective activity of specific edible fruits is limited. It was thus the goal of the inventors to develop edible fruit or extracts as nutraceutical products to protect the aging brain.

The genus *Passiflora* consist of about 500 species. Fifty to sixty species bear edible fruits, however, only a few are of commercial value, mainly *P. edulis*. The round to oval fruit contains several hundred seeds, each surrounded by an aromatic juicy aril. This semi-woody perennial climbing vine produces large attractive flowers resembling a crucifix to some Spanish monks who named it "passion fruit". Two major varieties, purple (*P. edulis* Sims *f. edulis*) and yellow (*P. edulis* Sims *f. flavicarpa* Deg.) passion fruit, are grown worldwide, mainly for juice production and fresh fruit. In Israel, the commercially grown cultivar "Passion Dream" (PD) is an F1 hybrid of a cross between these two varieties showing a combination of agriculturally important traits.

*P. edulis* has an extremely short juvenile phase in comparison to other fruit-providing species. The PD cultivar is self-fertile and from its seeds one can screen the F2 population from the original cross of the two varieties (yellow and purple). In the last 5 years the inventors have characterized close to 1000 F2 seedlings and in this F2 population there is variation in many important aspects including flowering time, climacteric behavior, taste and fruit size. While many traits are likely controlled by more than one gene, the color of fruit might be controlled by one locus since about 75% of the seedlings have purple colored fruit and 25% are yellow-green.

The unique aroma and flavor of passion fruit encouraged intensive research leading to the characterization of a broad spectrum of volatile constituents and attempts to synthesize them commercially [Murray, K., et al. (1972) Aust. J. of Chem. 25(1921-1933); Prestwich, G. D., et al. (1976) Tetrahedron 32:2945-2948; Scafato, P., et al. (2009) Chirality 21:176-182; Tominaga, T. and Dubourdieu, D. (2000) J. Agric. Food. Chem. 48:2874-2876; Werkhoff, P., et al. (1998) J. Agric. Food Chem. 46:1076-1093]. There is currently a revival of interest in the pharmaceutical industry, especially in Europe, in the use of the glycoside passiflorine, especially from *P. incarnata* L., as a sedative or tranquilizer. Italian chemists have extracted passiflorine from the air-dried leaves of *P. edulis*, and in Madeira, the juice of passion fruits is given as a digestive stimulant and treatment for gastric cancer.

The inventors have looked at variation among the select new lines they characterized with regard to the content of volatiles, using GCMS. Interesting differences were identified in levels of a group of thiol esters (sulfur containing volatiles) which were previously identified in passion fruit and shown to contribute to the distinct aroma associated with it: 3-mercaptohexyl acetate (3MHA), 3-mercaptohexyl butanoate and 3-mercaptohexyl hexanoate [Werkhoff, P., (1998) ibid.; Engel, K. and Tressl, R. (1991) J. Agric. Food Chem. 39:2249-2252]. Attempts were made by others to improve wine aroma by increasing levels of 3MHA [Swiegers, J., et al. (2007) Yeast 24:561-574]. A strong influence of the configuration of these chiral volatiles on their sensory properties has been demonstrated [Werkhoff, P., (1998) ibid.].

The inventors have screened such a population of passion fruits for lines that provide agriculturally important benefits (such as taste, yield, season), and examined the neuroprotective activity of these lines as well as the neuroprotective effect of the parent PD line. The surprising neuroprotective benefits of the passion fruit extracts, and specifically of the novel 428 cultivar, the inventors disclose here are applicable to many neurologic disorders and traumas.

More specifically, it is well established that elevated levels of extracellular glutamate are associated with neuronal damage and degeneration in brain disorders, including epilepsy, stroke and Parkinson's disease [Coyle, J. T. and Puttfarcken, P. (1993) Science 262(5134):689-695]. There are two defined mechanisms of glutamate cytotoxicity: the excitotoxicity and excitotoxicity-independent pathways. In the excitotoxicity pathway, superactivation of glutamate ionotropic receptors is followed by an increase in free intracellular calcium levels, and the generation of reactive oxygen species (ROS) in the cell [Savolainen, K. M., et al. (1998) Toxicol. Lett 102-103:363-367]. The excitotoxicity-independent process relies on an imbalance between oxidants and antioxidants in the cell (oxidative stress). Inhibition of cystine uptake via the $x_e^-$ cystine/glutamate antiporter system by glutamate leads to depletion in glutathione (GSH), the major intracellular antioxidant, and excessive production of ROS [Murphy, T. H., et al. (1989) Neuron 2(6):1547-1558]. There are evidence that these two pathways are activated in neuronal injuries [Tan, S., et al. (2001) Curr. Top. Med. Chem. 1(6):497-506]. An established in-vitro model system for investigating glutamate-oxidative-stress-mediated cell death is the immortalized mouse hippocampal cell line HT4, which phenotypically resembles neuronal precursor cells. Depletion in GSH and increased production of ROS in these cells are preceded by activation of c-Src and 12-Lox [Sen, C. K., et al. (2000) J. Biol. Chem. 275(17):13049-13055].

The inventors treated HT4 neuronal cells with chemicals that normally cause cell death by generating low levels of hydrogen peroxide flux or elevated levels of extracellular glutamate. Whereas extracts from the parent line gave relatively high protection, the F2 population segregated for protective ability with some lines giving low protection while other lines (such as line 428) giving even higher protection than both the PD parent line and NAC (N-acetyl cysteine), a known neuroprotective antioxidant. Thus, the inventors can breed and select lines presenting exceptionally high levels of neuro-protection. It should be noted that the inventors demonstrate here for the first time improved neuroprotective properties of passion fruit, specifically of the novel cultivar 428.

Age-associated neurodegenerative diseases, including Parkinson's disease, Alzheimer's disease, and vascular dementia are leading causes of mortality and disability worldwide. They do not have a cure and pose an enormous burden to caregivers, the health care system and society at large. With the aging of the world's population, and in the absence of effective pharmacological interventions, this problem is only expected to grow. Thus, there is an urgent need for new safe and efficacious intervention to prevent or mitigate neurodegenerative disease. The inventors provide herein passion fruit extracts, and specifically 428 and PD extracts, as neuroprotective functional foods, nutraceuticals, and for production of derivative pharmacological agents.

Thus, one object of the invention is providing a method for protection of neural cells from damage or deterioration in neural cell function using extracts of passion fruits. The invention further provides methods for prophylaxis, treatment, amelioration, inhibition or delaying the onset of neuro-pathological conditions using extracts of passion fruits.

Another object of the invention is providing neuroprotective compositions comprising passion fruit extracts, specifically of the new (428) and the parent PD cultivars extracts.

Yet another object of the invention is providing neuroprotective nutraceutical compositions comprising passion fruit extracts, specifically the newly-established 428 and PD cultivars extracts.

A further object of the invention is providing neuroprotective passion fruit extracts, specifically new (428) and PD cultivars extracts and uses thereof in treating neuro-pathologies.

These and other objects of the invention will become apparent as the description proceeds.

SUMMARY OF THE INVENTION

In the first aspect, the invention relates to a method for protection from, reduction, prevention or inhibition of neural cell damage or deterioration in neural cell function. The method comprises the step of contacting the neural cell with a botanical raw material (BRM) or an extract obtainable from passion fruits.

In the second aspect, the invention relates to a method for protection from, reduction, prevention or inhibition of neural cell damage or deterioration in neural cell function in a subject in need thereof. The method comprises the step of administering to the subject an effective amount of a botanical raw material (BRM) or an extract obtainable from passion fruits.

In the third aspect, the invention relates to a method for the treatment, prophylaxis, amelioration, inhibition or delaying the onset of a neuro-pathological condition. The method comprises the step of administering to a subject in need thereof an effective amount of a BRM or an extract obtainable from passion fruits.

In the fourth aspect, the invention relates to a botanical raw material (BRM) or an extract obtainable from passion fruits for use in the treatment, prophylaxis, amelioration, inhibition or delaying the onset of a neuro-pathological condition.

In another aspect, the invention relates to a composition for protection from, reduction, prevention or inhibition of neural cell damage or deterioration in neural cell function. The composition comprises a botanical raw material (BRM) or an extract of passion fruits, and optionally further comprises a pharmaceutically acceptable carrier, excipient or diluent.

In a further aspect, the invention relates to a composition for the treatment, prophylaxis, amelioration, inhibition or delaying the onset of a neuro-pathological condition in a subject. The composition comprises as an active ingredient a botanical raw material (BRM) or an extract of passion fruits.

In a further aspect, the invention relates to a nutraceutical composition comprising as an active ingredient a botanical raw material (BRM) or an extract obtainable from passion fruits.

In yet another aspect, the invention relates to a functional food comprising as an active ingredient a botanical raw material (BRM) or an extract obtainable from passion fruits.

These and other aspects of the invention will become apparent by the hand of the following figures.

BRIEF DESCRIPTION OF THE FIGURES

Characterization of the New *Passiflora* Cultivar 428

FIG. 1G: Acidity and levels of total soluble solids (TSS) in the parent PD and the F2 428 cultivars in summer and winter, during harvest, during storage in cold conditions, and after storage and shelf-life.

Abbreviations: D. Aft. Harv. (days after harvest); Hu.° (hue) (°); PD (Passion Dream); 428 (cultivar 428); Way. (nm) (wavelength (nm)); Absorp. (absorption); Lin. (line); Tot. edulans (p. ar.) (total edulans peak area); PD S. (PD summer); PD W. (PD winter); 428 S. (428 summer); 428 W. (428 winter); Ethyl. (l/L) (ethylene (l/L)); D. 12C (days at 12° C.); Harv. (harvest); Col. (cold conditions); AC (Acid); TSS (total soluble solids); Col.+SL. (cold conditions+shelf-life); LSD (least significant difference); TS/Ac. Rat. (Total soluble solids/Acid ratio); Bloom. Flow. (blooming flowers); Rip. Frui. (ripening fruits); Mont. (month); Wee. (week); Summ. (summer); Wint. (winter); Jan. (January); Feb. (February); Mar. (March); Apr. (April); Jun. (June); Jul. (July); Aug. (August); Sep. (September); Oct. (October); Nov. (November); Dec. (December).

Characterization of the New *Passiflora* Cultivar 428

Figure 2A:
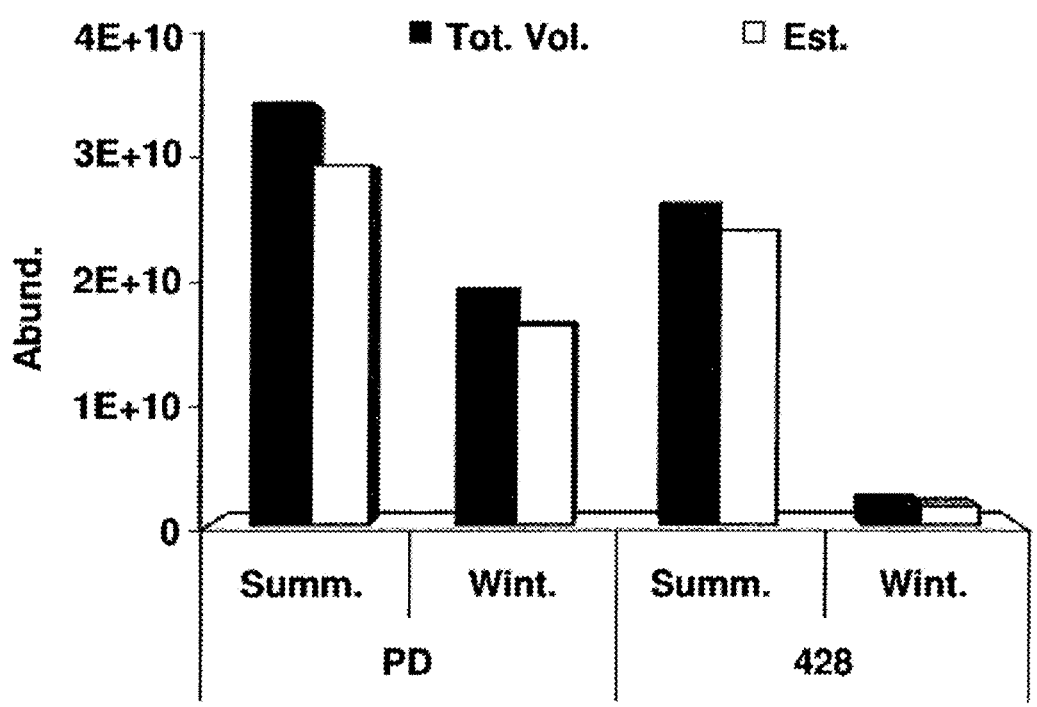

FIG. 2A: The total amount of volatiles produced by cultivars 428 and PD during summer and winter.

Figure 2B:
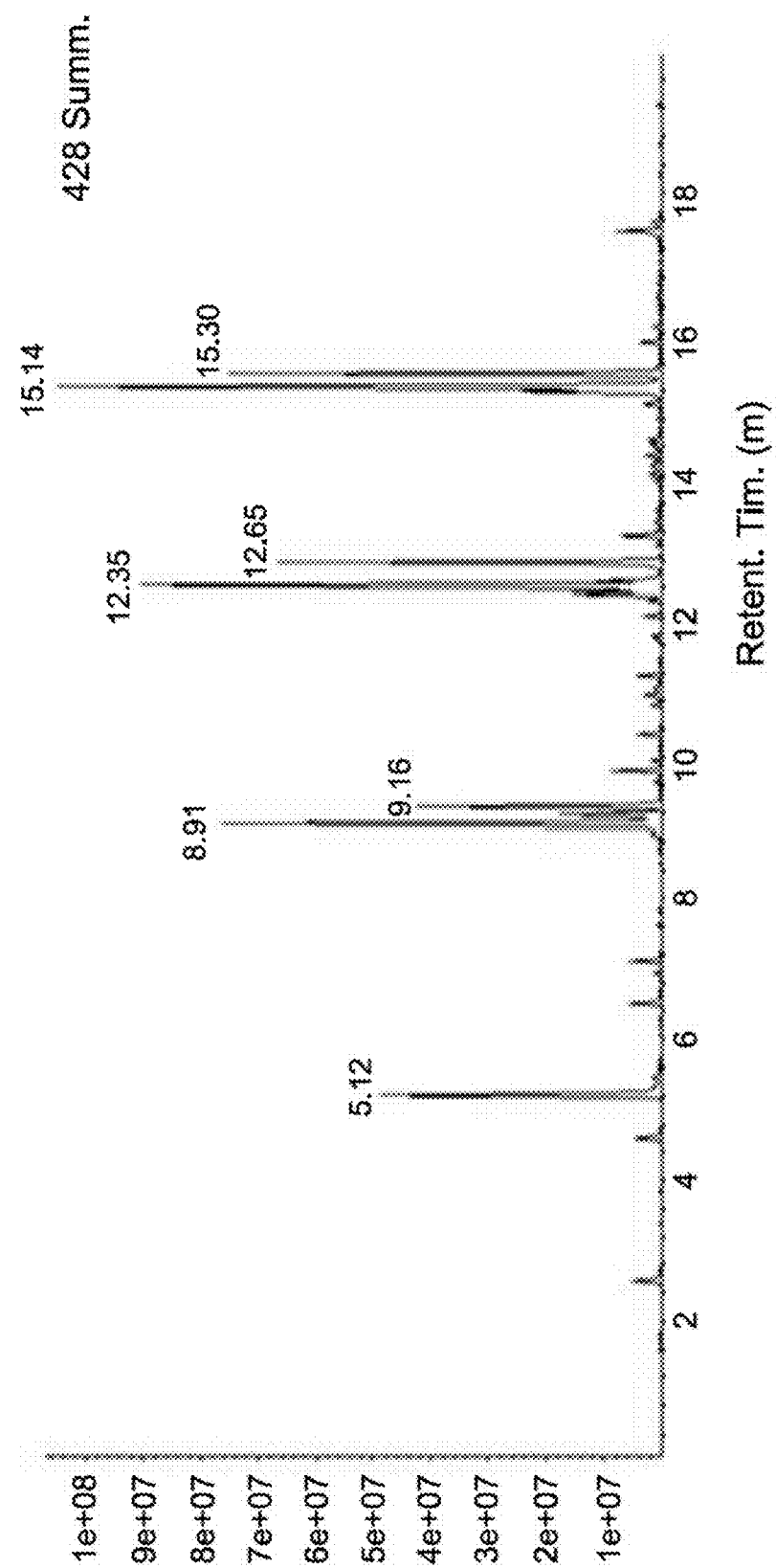

FIG. 2B: GCMS spectrum of passion fruit juice volatiles of cultivar 428 fruit harvested during summer.

FIG. 2C: GCMS spectrum of passion fruit juice volatiles of cultivar 428 fruit harvested during winter.

Figure 2D:
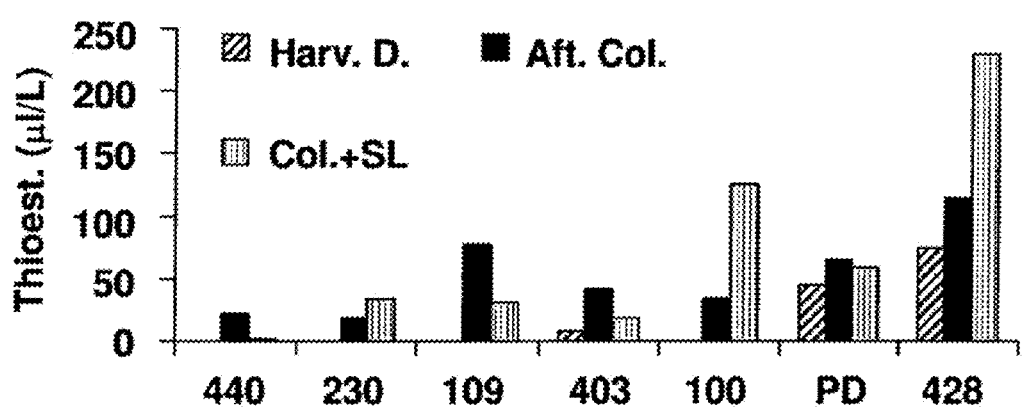

FIG. 2D: Thioesters content in cultivars 440, 230, 109, 403, 100, PD (Passion Dream) and 428 during harvest day, after storage in cold conditions and after storage in cold conditions and shelf life, as defined in the Experimental Procedures section.

Abbreviations: Abund. (abundance); Tot. Vol. (total volatiles); Est. (Esters); Thioest. (thioesters); Retent. Tim. (m) (retention time (minutes)); PD (Passion Dream); 428 (cultivar 428); Tot. Vol. (total volatiles); Summ. (summer); Wint. (winter); Harv. D. (harvest day); Aft. Col. (after cold conditions); Col.+SL. (cold conditions+shelf-life).

Effect of Different Passion Fruit Cultivars Extracts on Glucose Oxidase-Induced Cell Death HT-4 cells were exposed to 10% *Passiflora* fruit extracts from indicated cultivars and glucose oxidase 0.01 U/mL as a hydrogen peroxide generating system. Cell viability was evaluated 6 h after exposure by propidium iodide (PI) staining and measured by flow cytometry. Positive control cells were treated with NAC 20 mM for 6 hours. Data were collected from 5,000 cells.

Figure 3A:
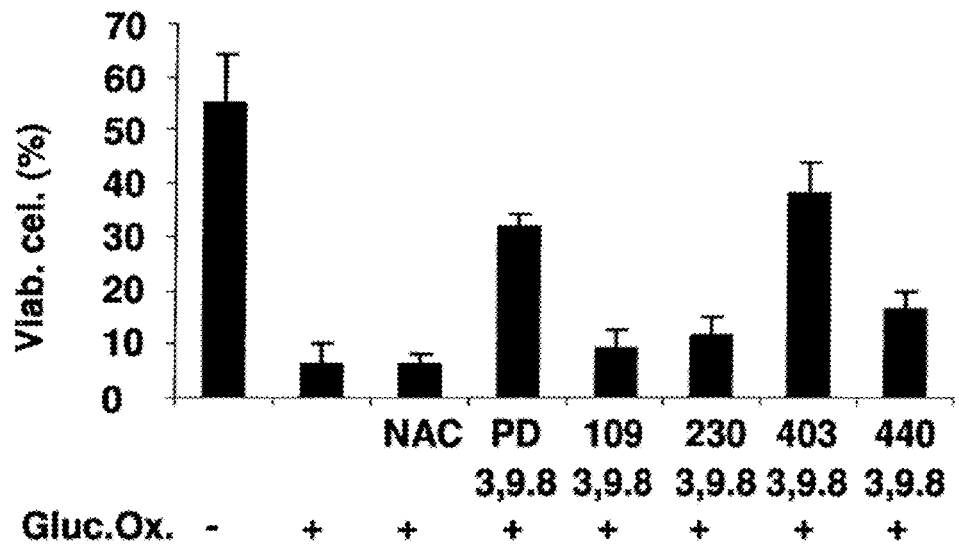

FIG. 3A: Viability of HT-4 cells exposed to 10% *Passiflora* fruit extracts (0.3 ml concentrate) from cultivars PD (Passion Dream), 109, 230, 403, and 440, and treated with glucose oxidase 0.01 U/mL.

Figure 3B:
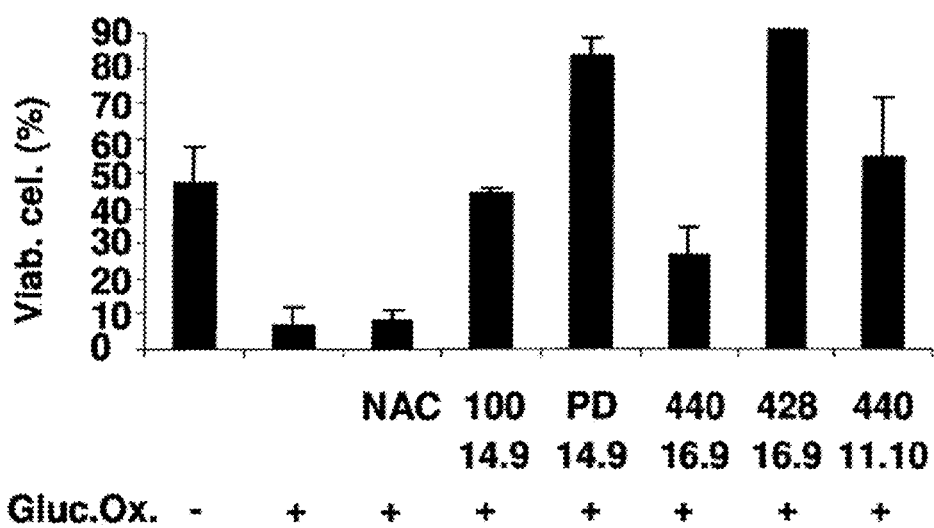

FIG. 3B: Viability of HT-4 cells exposed to 10% *Passiflora* fruit extracts from cultivars 100, PD, 428 and 440, and treated with glucose oxidase 0.01 U/mL.

Figure 3C:
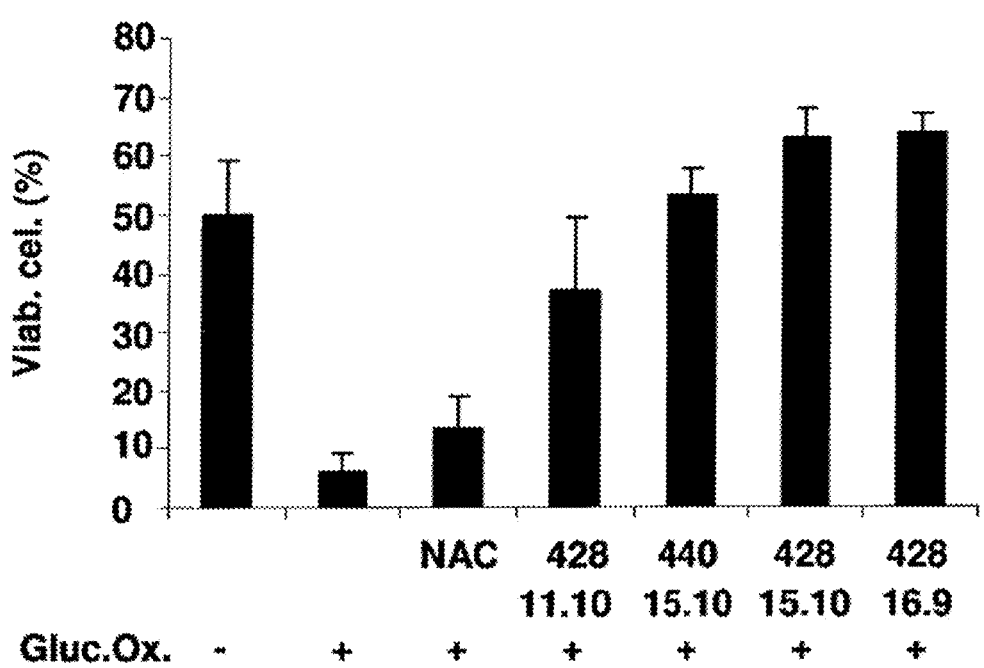

FIG. 3C: Viability of HT-4 cells exposed to 10% *Passiflora* fruit extracts from cultivars 428 and 440, and treated with glucose oxidase 0.01 U/mL.

Values are means±SD (n=3 for each group); The digits below cultivars are harvest dates (for example, 3, 9.8 refers to August 3 and 9).

Abbreviations: Viab. cel. (%), cell viability (%); Gluc. Ox., glucose oxidase; NAC (N-acetyl cysteine); PD (passion dream cultivar).

Figure 4A:
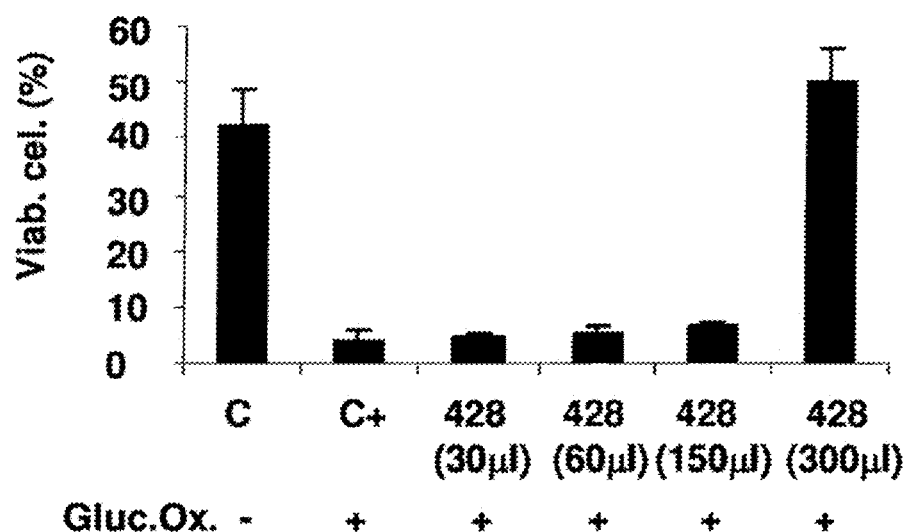

Dose-Dependent and Heat-Labile Protective Effect of PD (Passion Dream) and New (428) *Passiflora* Cultivars FIG. 4A: HT-4 cells were concomitantly exposed to glucose oxidase 0.01 U/mL and different volumes (30 L, 60 L, 150 L and 300 L) of extract (concentrate) from the new (428) passion fruit cultivar for 6 hours. Cell viability was evaluated using PI and flow cytometry.

Figure 4B:
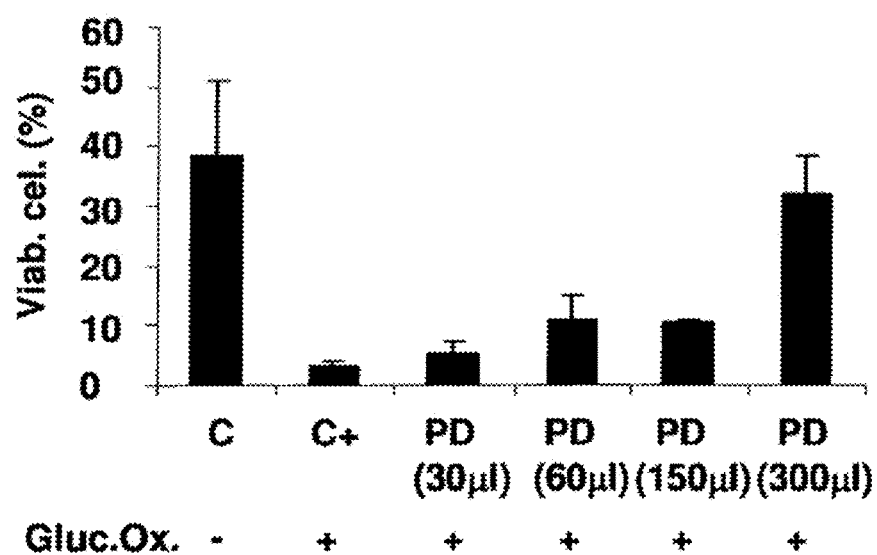

FIG. 4B: HT-4 cells were concomitantly exposed to glucose oxidase 0.01 U/mL and different volumes (30 L, 60 L, 150 L and 300 L) of extracts (concentrate) from the PD passion fruit cultivar for 6 hours. Cell viability was evaluated using PI and flow cytometry.

Figure 4C:
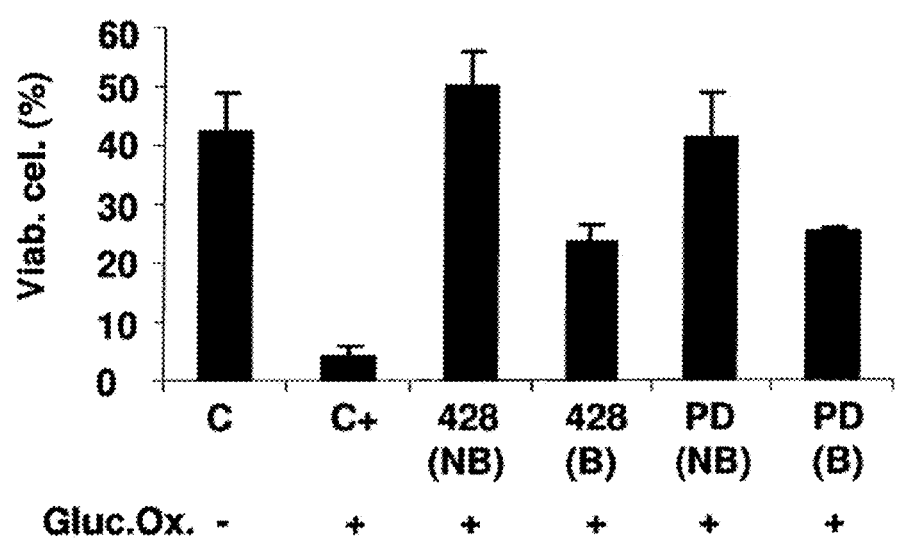

FIG. 4C: HT-4 cells were concomitantly exposed to glucose oxidase 0.01 U/mL and boiled (B) or unboiled (NB) extracts (concentrate) from PD or 428 cultivars fruits for 6 hours. Cell viability was evaluated using PI and flow cytometry.

Values are means±SD (n=3 for each group).

Abbreviations: Viab. cel. (%), cell viability (%); Gluc. Ox., glucose oxidase; B, boiled; NB, not boiled; C (control); PD (Passion Dream).

Effect of PD (Passion Dream) or New (428) Passion Fruit Cultivars Extracts on Glutamate-Induced Cell Death and on ROS Production FIG. 5A: HT-4 Cells exposed to glutamate and to 0.3 ml extract (concentrate) of PD or 428 passion fruit cultivars for 24 hours. Cell viability evaluated using PI and flow cytometry.

FIG. 5B: HT-4 cells exposed to 0.3 ml extract (concentrate) from PD or 428 passion fruit cultivars for 6 hours. ROS production evaluated by flow cytometry detecting DCF fluorescence level. Values are means±SD (n=3 for each group).

Abbreviations: Viab. cel. (%), cell viability (%); C (control); PD (Passion Dream); Frui Ext. (fruit extract); Glu. (Glutamate); DCF Flou. (DCF Florescence).

DETAILED DESCRIPTION OF THE INVENTION

Neurodegeneration is a common theme of many nervous system diseases and disorders, such as Alzheimer's disease, Parkinson's disease, ALS, head trauma, epilepsy and stroke. These disorders are devastating and their management expensive, with annual costs currently exceeding several hundred billion dollars in the United States alone, and current treatments are inadequate. Adding to the urgency of the problem is the fact that the incidence of these age-related disorders is increasing rapidly as population demographics change.

A common theme of these diseases and disorders is the loss of neural cell functions and/or neural cell death. Here, the inventors disclose methods for neuro-protection and thereby prevention and treatment of pathologies which cause neural cell deterioration and death, involving exposing neural cells, whether directly or through administration to a patient, to botanical raw material (BRM) or an extract obtainable from passion fruits. The inventors also disclose compositions comprising botanical raw material (BRM) or an extract obtainable from passion fruits, and nutraceutical compositions comprising the same. The inventors demonstrate here the efficacy of these methods and compositions in the protection of neural cells in conditions simulating neurodegenerative disease.

Thus, in the first aspect, the invention relates to a method for protection from, reduction, prevention or inhibition of neural cell damage or deterioration in neural cell function. The method comprises the step of contacting the neural cell with a botanical raw material (BRM) or an extract obtainable from passion fruits.

When referring to cell damage, the term "damage" relates to any disruption of physiological cell functions or cell death. Non-limiting examples for disruption of physiological cell functions include: oxidative stress (for example, lipid peroxidation, DNA and RNA oxidation and protein oxidation), non-specific glycation, protein misfolding, DNA mutation, loss of any cellular structure integrity, metabolic stress, ionizing and non-ionizing radiation damage and chemical stress (for example, exposure to acid or basic substances).

Accordingly, the expression "protection from neural cell damage or deterioration in neural cell function" means either preventing or decreasing neural death, or preventing or decreasing the deterioration in neural function (as exemplified for instance by secretion of neurotransmitters, dendrite and axonal growth, transfer of electrical impulses, response to stimuli, maintaining structural integrity of myelin sheaths and Ranvier's nodes, etc.) as compared to control neural cells not treated by the extract of the passion fruits. Such reduced cell death is demonstrated in FIG. 5A and Example 4, where application of the BRM according to the method of the invention inhibited cell death induced by glutamate toxicity. Expressing the ruction of cell death as percent change in viability relative to control untreated and unchallenged cells [(% change in viability)/% (viability in control cells)], ceteris paribus, the reduced cell death as compared to untreated cells may be at least about 1% to about 99%, 2% to about 98%, 3% to about 97%, 4% to about 96%, 5% to about 95%, 6% to about 94%, 7% to about 93%, 8% to about 92%, 9% to about 91%, 10% to about 90% or 11% to about 89%, 12% to about 88%, 13% to about 87%, 14% to about 86%, 15% to about 85%, 16% to about 84%, 17% to about 83%, 18% to about 82%, 19% to about 81%, 20% to about 80%, 21% to about 79%, 22% to about 78%, 23% to about 77%, 24% to about 76%, 25% to about 75%, 26% to about 74%, 27% to about 73%, 28% to about 72%, 29% to about 71%, 2% to about 70%, 32% to about 69%, 33% to about 68%, 34% to about 67%, 35% to about 66%, 36% to about 65%, 37% to about 64%, 38% to about 63%, 39% to about 62%, 40% to about 61%, 41% to about 60%, 42% to about 59%, 43% to about 58% or 44% to about 57%.

The decrease in neural cell death or neural function loss may be of about 1% to about 99%, 2% to about 98%, 3% to about 97%, 4% to about 96%, 5% to about 95%, 6% to about 94%, 7% to about 93%, 8% to about 92%, 9% to about 91%, 10% to about 90% or 11% to about 89%, 12% to about 88%, 13% to about 87%, 14% to about 86%, 15% to about 85%, 16% to about 84%, 17% to about 83%, 18% to about 82%, 19% to about 81%, 20% to about 80%, 21% to about 79%, 22% to about 78%, 23% to about 77%, 24% to about 76%, 25% to about 75%, 26% to about 74%, 27% to about 73%, 28% to about 72%, 29% to about 71%, 2% to about 70%, 32% to about 69%, 33% to about 68%, 34% to about 67%, 35% to about 66%, 36% to about 65%, 37% to about 64%, 38% to about 63%, 39% to about 62%, 40% to about 61%, 41% to about 60%, 42% to about 59%, 43% to about 58% or 44% to about 57%. More specifically, a decrease in neural cell death or neural function loss may be of about 1%, 5%, 10%, 15%, 20%, 25%, 30%, 35%, 40%, 45%, 50%, 55%, 60%, 65%, 70%, 75%, 80%, 85%, 90%, 95% or 100%.

The expression "reduction" and "inhibition" of neural cell damage or deterioration in neural cell function relate to the retardation, lessening or attenuation of a process which inflicts neural cell damage and/or affects neural cell activity detrimentally. Such reduction includes reduction by any one of about 1% to about 99%, 2% to about 98%, 3% to about 97%, 4% to about 96%, 5% to about 95%, 6% to about 94%, 7% to about 93%, 8% to about 92%, 9% to about 91%, 10% to about 90% or 11% to about 89%, 12% to about 88%, 13% to about 87%, 14% to about 86%, 15% to about 85%, 16% to about 84%, 17% to about 83%, 18% to about 82%, 19% to about 81%, 20% to about 80%, 21% to about 79%, 22% to about 78%, 23% to about 77%, 24% to about 76%, 25% to about 75%, 26% to about 74%, 27% to about 73%, 28% to about 72%, 29% to about 71%, 2% to about 70%, 32% to about 69%, 33% to about 68%, 34% to about 67%, 35% to about 66%, 36% to about 65%, 37% to about 64%, 38% to about 63%, 39% to about 62%, 40% to about 61%, 41% to about 60%, 42% to about 59%, 43% to about 58% or 44% to about 57%. More specifically, such reduction includes reduction by any one of about 1%, 5%, 10%, 15%, 20%, 25%, 30%, 35%, 40%, 45%, 50%, 55%, 60%, 65%, 70%, 75%, 80%, 85%, 90%, 95% or 100%.

Moreover, with regards to the above, it is to be understood that, where provided, percentage values such as, for example, 10%, 50%, 120%, 500%, 1000%, 2000% etc., are interchangeable with "fold change" values, i.e., 0.1, 0.5, 1.2, 5, etc., respectively.

The term "prevent", "prevention", "prophylaxis" and all variations of this term is intended to mean the countering in advance of neural cell damage or deterioration in neural cell function. In this case it is understood that the passion fruit extract, or any composition thereof is applied prior to the initiation, or during the early stages of, a process or an action which involves such neural cell damage or deterioration in neural cell function. The term "neural cell function" relates to any normal physiological cellular activity, depending on the specific cell type. Non-limiting examples of such functions include cell viability, secretion of neurotransmitters, dendrite and axonal growth, transfer of electrical impulses and response to stimuli in neurons, maintaining structural integrity of myelin sheaths and Ranvier's nodes in oligodendrocytes and Schwann cells, and supplying nutrients and oxygen, and recycling neurotransmitters in astrocytes.

Conversely, the protection afforded by the methods and compositions of the invention may, in fact, promote viability and survival of cells. For example, cells protected according to said method and exposed to toxic stress may display higher survival rates than unprotected cells exposed to said stress. Furthermore, cells protected according to said method may display higher viability rates than untreated cells. Such enhanced viability is demonstrated, for instance, in FIGS. 3B, 3C, 4A and 4C, where application of the BRM according to the method of the invention enhanced cellular viability, even in the face of concomitant oxidative stress. Expressing enhanced viability as percent change in viability relative to control untreated and unchallenged cells [(% change in viability)/%(viability in control cells)], ceteris paribus, the increase in viability and survival as compared to untreated cells may be at least about 1% to about 99%, 2% to about 98%, 3% to about 97%, 4% to about 96%, 5% to about 95%, 6% to about 94%, 7% to about 93%, 8% to about 92%, 9% to about 91%, 10% to about 90% or 11% to about 89%. Alternatively, the increase in viability and survival as compared to untreated cells may be at least about 11%, at least about 15%, at least about 20%, at least about 30%, at least about 40%, at least about 50%, at least about 60%, at least about 70%, at least about 80%, at least about 89%, at least about 99% or at least about 100%.

As mentioned above, the method of the invention comprises the step of contacting neural cells with the BRM or extract according to the invention. In should be understood that the term "increase" means herein the augmentation, boosting, amplifying, raising or enhancing of a specific object or quality, wherein said increase may be of about 1% to 2%, about 2% to 3%, about 3% to 4%, about 4% to 5%, about 5% to 6%, about 6% to 7%, about 7% to 8%, about 8% to 9%, about 9% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85%, about 85% to 90% or about 95% to 100%.

It is understood that the term "contacting" is interpreted herein as placing in direct communication, i.e., bringing to physical interaction. For example, the BRM or extract of the invention may be applied directly to neural cells. It is further understood that such contacting is performed under conditions suitable for said neural cells survival, for example, the suitable temperature, moisture, pH and nutrients concentrations.

Throughout this specification, the term "neural cell" relates to cells that may be any one of central nervous system neurons and glial cells, astrocyte, neuron cells, oligodendrocyte, Schwann cells, satellite cells, spindle cells, neuronauditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells of eye, photoreceptor green-sensitive cone cells of eye, photoreceptor red-sensitive cone cells of eye, proprioceptive primary sensory neurons, touch-sensitive primary sensory neurons, type I carotid body cells, type II carotid body cells, type I hair cells of vestibular apparatus of ear, type II hair cells of vestibular apparatus of ear, type I taste bud cells, autonomic neuron cells, cholinergic neural cells, adrenergic neural cells, peptidergic neural cells, sense organ and peripheral neuron supporting cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells and enteric glial cells.

As shown by the following examples, the method of the invention uses BRM obtained from passion fruit, thus, the above cells may be contacted, for example, with botanical raw material. "Botanical raw material" is defined herein as a fresh or processed (e.g., cleaned, frozen, dried, or sliced) part of a single species of plant; for example, a fresh or processed fruit of passion fruit. Generally, said part of a single species of plant may be any one of fruits, flowers, seeds, leaf disks, roots, stems, shoots, leaves, pollen, embryos, cotyledons, hypocotyls, megagametophytes, callus tissue and meristematic tissue. More specifically, the plant part may be any one of fruits, juice, fruit skin, pulp and seeds, most specifically fruit-juice. Processed botanical raw material may include shredded, macerated, ground, dissolved, squeezed, filtered, crushed or otherwise mechanically manipulated parts of a plant material.

In more specific embodiment, BRM or extract may be any one of a juice, fruit skin, pulp or seeds obtained from at least one variety or cultivar of passion fruits or a mixture of two or more cultivars of passion fruits, or any concentrate or preparation obtained from said juice, fruit skin, pulp, seeds or fruits.

The term "extract" or "botanical extract" as used herein refers to a product prepared by separating, by chemical or physical process, medicinally active portions of a plan from the inactive or inert components. More specifically, extraction of passion fruits may be performed in many ways known to the skilled man. For example, the passion fruit pulp (including seeds) or juice may be acquired by juicing the fruits and squeezing the material obtained into a gauze pad, filtering clear juice into test tubes that are then stored at −20° C. Prior to freezing or after thawing, the juice may be further clarified by centrifugation. Specific example is centrifugation at 12,000 RPM for 5 minutes and collection of the clear supernatant. In yet another embodiment, the passion fruit extract may be obtained by juicing and manufacturing processes.

Thus, it is understood that the botanical raw material (BRM) or extract obtainable from passion fruits may be used according to the invention to ameliorate or prevent neural cell disorders or damage. FIGS. 3A-3C in Example 3 show the protection of neural cells from oxidative stress induced by glucose oxidase, afforded to cells treated with the BRM, and specifically BRM from cultivar 428 (FIGS. 3B and 3C). Indeed, cells treated with the BRM exhibit lower mortality under oxidative stress as compared to untreated cells. FIG. 5B demonstrates that the BRM effectively lowers cellular ROS levels. FIG. 5A shows that the BRM is also effective in preventing cell death due to glutamate toxicity.

Since the passion fruit BRM or extract of the invention provides protection against neural cell damage, as demonstrated in Examples 3 and 4, they may be used to protect organisms comprising such cells. Therefore, in the second aspect, the invention provides a method for protection from, reduction, prevention or inhibition of neural cell damage or deterioration in neural cell function in a subject in need thereof. This method comprises the step of administering to the subject an effective amount of a botanical raw material (BRM) or an extract obtainable from passion fruits.

The terms "subject," and "patient," used interchangeably herein, refer to an animal, specifically a mammalian (including a non-primate and a primate) including, but not limited to, murines, simians, humans, mammalian farm animals (e.g., bovine, porcine, ovine), mammalian sport animals (e.g., equine), and mammalian pets (e.g., canine and feline), specifically the term refers to humans. In a certain embodiment, the subject, specifically a mammal, more specifically a human, is further characterized with neural cell damage, deterioration in neural cell function, or a neuro-pathological condition. Alternatively, the subject suffers from abnormal neurite outgrowth and fasiculation of nerves.

According to the methods of the invention, an "effective amount" of BRM or extract of the invention is used to produce the desired results, i.e., cellular protection, amelioration of cell damage, etc. The term "effective amount" as used herein is an amount which is determined by considerations known to the man of skill in the art. The amount must be sufficient to protect from, reduce, prevent or inhibit neural cell damage or deterioration in neural cell function in a subject in need thereof. Dosing is dependent on the severity of the symptoms and on the responsiveness of the subject to the administered composition. Medically trained professionals can easily determine the optimum dosage, dosing methodology and repetition rates. In any case, the attending physician, taking into consideration the age, sex, weight and state of the disease of the subject to be treated, will determine the dose. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the composition of the invention in bodily fluids or tissues. Following successful treatment, it may be desirable to have the patient undergo maintenance therapy to prevent the recurrence of the disease state, wherein the composition of the invention is administered in maintenance doses, once or more daily, weekly, monthly or yearly, or even once every 2 to 20 years.

Therefore, the invention discloses a method employing botanical raw material (BRM) or an extract obtainable from passion fruits to ameliorate neural cell damage or deterioration in neural cell function in subjects suffering from such damage or deterioration, and to prevent such damage and deterioration or any pathologic condition associated therewith in healthy subjects.

Accordingly, in one embodiment, the invention provides a method for protection from, reduction, prevention or inhibition of neural cell damage or deterioration in neural cell function in a subject in need thereof, wherein the subject suffers of a neuro-pathological condition.

As used herein by the methods and compositions of the invention, the terms "pathologic condition", "condition", "disease", "disorder", and "illness", refer to a conditions in which there is a disturbance of normal functioning. Such condition is any abnormal condition of the body or mind that causes discomfort, dysfunction, or distress to the person or subject affected or those in contact with the person or subject. Sometimes the term is used broadly to include injuries, disabilities, syndromes, symptoms, deviant behaviors, and atypical variations of structure and function, while in other contexts these may be considered distinguishable categories.

Since the invention provides methods for protection from, reduction, prevention or inhibition of deterioration in neural cell function in a subject in need thereof, it is important to clearly define the scope of the term "neural cell function". Herein, this term relates to any normal physiological cellular activity, depending on the specific cell type. Non-limiting examples of such functions include cell viability, secretion of neurotransmitters, dendrite and axonal growth, transfer of electrical impulses and response to stimuli in neurons, maintaining structural integrity of myelin sheaths and Ranvier's nodes in oligodendrocytes and Schwann cells, and supplying nutrients and oxygen, and recycling neurotransmitters in astrocytes. The passion fruit extracts and BRM of the invention are therefore particularly suitable for the amelioration and prevention not only neuronal cell disorders, but also disorders afflicting other neural cell types, a list thereof is provided herein.

The term "neuro-pathological condition" relates to any pathological condition caused by, or which causes, or is associated with neural cell disorders, such as any deterioration of the neural cell functions or viability. As explained herein, such conditions may be ischemic diseases, neurodegenerative disorders, brain traumas, metabolic disorders which affect the nervous system, such as diabetes and phenylketonuria, immunological disorders which affect the brain, such as Hashimoto's Thyroiditis, genetic diseases which affects neural cells, such as Tay-Sachs disease, metachromatic leukodystrophy, Krabbe disease, Fabry disease, Gaucher disease, Farber disease, and Niemann-Pick disease, nutrient deficiencies such as vitamin $B_6$ and D deficiencies, and any sequelae which affects the nervous system.

It should be further appreciated that the methods and compositions of the invention may be applicable for treating neuro-pathological and neurodegenerative disorders or of any pathologic condition associated therewith. It is understood that the interchangeably used terms "associated", linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology. Such conditions may include for example, Alzheimer's disease, Parkinson's disease, amyotrophic lateral sclerosis, head trauma, epilepsy, stroke, neuromyotonia/Isaacs syndrome, lower motor neuron lesion, Werdnig-Hoffman disease, amyotrophic lateral sclerosis, Kennedy disease, organophosphate poisoning, benzodiazepine withdrawal, magnesium deficiency, myalgic encephalomyelitis, dehydration, fatigue, lyme disease, myasthenia gravis, rabies, fibromyalgia, subarachnoid hemorrhage, intracerebral hemorrhage, occlusion and stenosis of precerebral arteries, occlusion and stenosis of basilar artery, occlusion and stenosis of carotid artery, occlusion and stenosis of vertebral artery, occlusion of cerebral arteries, cerebral thrombosis with or without cerebral infarction, cerebral embolism with or without cerebral infarction, transient cerebral ischemia, basilar artery syndrome, vertebral artery syndrome, subclavian steal syndrome, vertebrobasilar artery syndrome, transient ischemic attack (TIA), cerebral atherosclerosis, hypertensive encephalopathy, cerebral aneurysm, cerebral arteritis, Moyamoya Disease, nonpyogenic thrombosis of intracranial venous sinus, atherosclerosis, atherosclerosis of renal artery, atherosclerosis of native arteries of the extremities, intermittent claudication, aortic aneurysm, dissection of aorta, dissection of carotid artery, dissection of iliac artery, dissection of renal artery, dissection of vertebral artery, erythromelalgia, and polyarteritis nodosa.

In one specific embodiment, the passion fruit BRM or extracts used by the methods of the invention are of at least one of a cultivar designated 428 and a cultivar designated Passion Dream (PD), or any crosses or progeny thereof.

A cultivar is a plant or group of plants selected for desirable characteristics that can be maintained by propagation. The International Union for the Protection of New Varieties of Plants (UPOV—French: Union internationale pour la protection des obtentions végétales) offers legal protection of plant cultivars to people or organisations who introduce new cultivars to commerce. UPOV requires that a cultivar be distinct, uniform and stable. Most cultivars have arisen in cultivation but a few are special selections from the wild. To be distinct, it must have characteristics that easily distinguish it from any other known cultivar. To be uniform and stable, the cultivar must retain these characteristics under repeated propagation. A specifically suitable cultivar to be used according to the methods of the invention and for producing the extracts, BRM or any compositions thereof according to the invention is cultivar 428, also called "Dena" and "RS" as well as the parent PD cultivar.

PD is a cultivar which is an F1 hybrid of a cross between the two edible major varieties of *Passiflora, P. edulis* Sims *f. edulis* and *P. edulis* Sims *f. flavicarpa* Deg. Thus, the expression "a cultivar designated 428 and a cultivar designated Passion Dream (PD), or any crosses or progeny thereof" is intended to relate to each of the two cultivars (428 and PD), or any generation of a passion fruit plant which is the product of a sexual mating between member of each cultivars with themselves or with the other cultivar. The sexual mating may be between different plants in different cultivars, different plants in the same cultivar, or even the same plant in the same cultivar.

In a more specific embodiment, the BRM or extract used by the method of the invention may be obtained from passion fruits of a cultivar designated 428, or any crosses or progeny thereof.

Figure 1A:
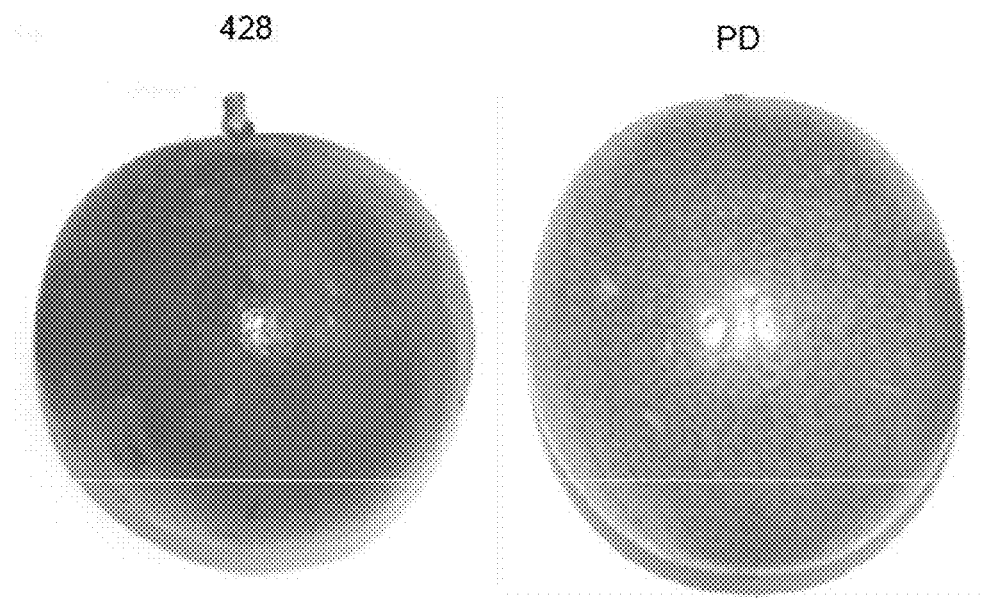
FIG. 1A: Photograph of 428 and PD cultivar fruits. 428 presents with rounder and smaller fruits than the parent PD.

Cultivar 428 is indeed distinct, as explained in Example 1 and 2 herein. The Examples show that cultivar 428 (herein:

'428') has a distinct fruit color and shape (FIGS. 1A and 1B, respectively), demonstrates different blooming behavior (FIG. 1C), has a high carotenoid content as compared to PD and cultivar 230 (FIG. 1E), produces no edulans (FIG. 1D) and very little or no ethylene (FIG. 1F), has a higher acid content (especially during winter time; FIG. 1G) and an extremely low volatiles and esters content during winter time (FIGS. 2A-2D).

It is appreciated that cultivar 428 refers to a cultivar of the *Passiflora* plant also called "Dena" and "RS", for which an application for Breeder's Rights was filed in Israel on Nov. 7, 2010.

It should be noted that in order to produce identical plants of the same genotype of PD or 428 the plants are vegetatively propagated by inducing adventious root formation in cut branches. Within a fruit of either cultivar, even if fertilized by pollen coming from the same flower, the seed contain embryos that are genetically diverse. Thus, planting the seeds will raise seedlings with different genotypes and phenotypes. If PD or 428 ovules are fertilized by pollen coming from a different cultivar or genotype, clearly the seeds will contain embryos with a new combination of genetic information, some originating from 428 or PD. Aside from vegetative propagation, it is understood that "428" also refers to lines produced by selfing and/or outcrossing of said cultivar 428. For example, new genotypes of *Passiflora* plants can be produced by planting the seeds of the *Passiflora* plant cultivar 428 from fruit resulting from self or cross pollination, with adequate isolation using standard techniques well known to an artisan skilled in the agricultural arts. Seeds can be harvested from such a plant using standard, well known procedures. All resulting progeny are also considered 428.

As all progeny of sexual reproduction, *Passiflora* 428 cultivar seeds are naturally variable due to genetic segregation. Thus, it is emphasized that those progeny which bud from said seeds and exhibit identical or superior neuroprotective, prophylactic or therapeutic qualities as compared to those traits demonstrated here shall also be considered to be cultivar 428, and are therefore encompassed by the present invention.

Conversely, and as indicated herein above, in order to maintain a constant, essentially variation-free 428 line, the 428 may be vegetatively propagated (rather than seeded). The plants formed from this vegetative propagation are also considered as cultivar 428 herein.

A cultivar is not the same as a botanical variety, and there are differences in the rules for the formation and use of the names of botanical varieties and cultivars. In botanical nomenclature, variety is a taxonomic rank below that of species: as such, it gets a three-part infraspecific name. A variety will have an appearance distinct from other varieties, but will hybridize freely with those other varieties (if brought into contact). Usually varieties will be geographically separate from each other.

In more specific embodiments of the method for protection from, reduction, prevention or inhibition of neural cell damage or deterioration in neural cell function, as well as in a subject in need thereof, the BRM or an extract obtainable from passion fruits may be any one of a juice, fruit skin, pulp or seeds obtained from at least one variety or cultivar of passion fruits. The BRM or an extract may also be a mixture of two or more cultivars of passion fruits, or any concentrate or preparation obtained from the juice, fruit skin, pulp, seeds or whole fruits.

In one specific embodiment, the extract or BRM may be obtained from passion fruit juice.

The BRM or extract mixture according to the methods and compositions (described herein after) of the invention may comprise components or material, specifically, BRM, from two or more cultivars of passion fruits, such as, for example: cultivars 428 and PD, cultivars 428 and 440, cultivars 428 and 403, cultivars 428 and 230, cultivars 428 and 103, cultivars 428 and 109, cultivars PD and 440, cultivars PD and 403, cultivars PD and 230, cultivars PD and 103, cultivars PD and 109, cultivars 440 and 403, cultivars 440 and 230, cultivars 440 and 103, cultivars 440 and 109, cultivars 403 and 230, cultivars 403 and 103, cultivars 403 and 109, cultivars 230 and 103, cultivars 230 and 109, and cultivars 109 and 103, or combinations of three or more cultivars in a mixture, such as cultivars 428, PD and 440, cultivars 428, PD and 403, cultivars 428, PD and 230, cultivars 428, PD and 103 and cultivars 428, PD and 109, or of any crosses or progeny thereof, wherein the w/w ratio between every two cultivars in said mixtures may be between about 1:1,000,000 to about 1:500,000, about 1:500,000 to about 1:100,000, about 1:100,000 to about 1:50,000, about 1:50,000 to about 1:10,000, about 1:10,000 to about 1:1,000, about 1:1,000 to about 1:500, about 1:500 to about 1:100, about 1:100 to about 1:50, about 1:50 to about 1:25, about 1:25 to about 1:10 or about 1:10 to about 1:1.

In a further embodiment of the method according to the invention, the BRM or extract of passion fruits, or any mixtures thereof as described herein, reduces at least one of radical cellular oxygen species (ROS) levels, oxygen species toxicity and glutamate toxicity. More specifically, as shown by FIG. 5B, treating cells with the extract or BRM of the invention lead to a clear decrease in ROS production. Therefore, in one specific embodiment, treatment according to the invention leads to reduction of ROS levels in the treated cells. In yet another embodiment, treatment with the BRM or extracts of the invention results in decrease of ROS levels in the treated subject.

Reactive oxygen species (ROS) are chemically-reactive molecules containing oxygen. Reactive oxygen species are highly reactive due to the presence of unpaired valence shell electrons. ROS form as a natural byproduct of the normal metabolism of oxygen and have important roles in cell signaling and homeostasis. However, during times of environmental stress (e.g., UV or heat exposure), ROS levels can increase dramatically. This may result in significant damage to cell structures. This cumulates into a situation known as oxidative stress. ROS are also generated by exogenous sources such as ionizing radiation. Examples of ROS include oxygen ions and peroxides.

In general, harmful effects of reactive oxygen species on the cell are most often damage of DNA, oxidations of polydesaturated fatty acids in lipids (lipid peroxidation), oxidations of amino acids in proteins and oxidatively inactivate specific enzymes by oxidation of co-factors.

Oxygen toxicity is a condition resulting from the harmful effects of exposure to molecular oxygen ($O_2$) at elevated partial pressures. It is also known as oxygen toxicity syndrome, oxygen intoxication, and oxygen poisoning. Severe cases can result in cell damage and death, with effects most often seen in the central nervous system, lungs and eyes. Oxygen toxicity is a concern for scuba divers, those on high concentrations of supplemental oxygen (particularly premature babies), and those undergoing hyperbaric oxygen therapy. The result of breathing elevated concentrations of oxygen is hyperoxia, an excess of oxygen in body tissues. The body is affected in different ways depending on the type of exposure. Central nervous system toxicity is caused by short exposure to high concentrations of oxygen at greater than atmospheric pressure. Symptoms may include disorientation, breathing problems, and vision changes such as myopia. Prolonged or very high oxygen concentrations can cause oxidative damage to cell membranes, the collapse of the alveoli in the lungs, retinal detachment, and seizures.

In the context of neural cells, a major contributor to ROS production is, under certain circumstances, glutamate. Glutamate toxicity is mediated through superactivation of glutamate ionotropic receptors followed by an increase in free intracellular calcium levels, and the generation of reactive oxygen species (ROS) in the cell, and by inhibition of cystine uptake, leading to depletion of cellular glutathione (GSH) and the consequent excessive production of ROS.

The inventors present here methods and compositions that protect neural cells from damage, deterioration in function and death. Since these phenomena are characteristic of neuro-pathological disorders, and especially neurodegenerative diseases, the invention also envisages compositions and methods for the treatment of such diseases accordingly.

Therefore, in the third aspect, the invention is directed to a method for the treatment, prophylaxis, amelioration, inhibition or delaying the onset of a neuro-pathological condition. The method comprises the step of administering to a subject in need thereof an effective amount of a BRM or an extract obtainable from passion fruits.

The term "Treating" is used herein to refer to any treatment of, or prevention of, or inhibition of a disorder or disease in a subject and includes by way of example: (a) preventing the disease or disorder from occurring in a subject that may be predisposed to the disease or disorder, but has not yet been diagnosed as having it; (b) inhibiting the disease or disorder, i.e., arresting or delaying its progression; or (c) relieving or ameliorating the disease or disorder, i.e., causing regression. More specifically, "treating" refers to inhibiting, preventing or arresting the development of pathology (e.g., a neuro-pathological condition, neural cell death, deterioration of neural cell function, abnormal neurite growth and nerve fasiculation) and/or causing the reduction, remission, or regression of a pathology. Those of skill in the art will understand that various methodologies and assays can be used to assess the development of pathology, and similarly, various methodologies and assays may be used to assess the reduction, remission or regression of a pathology. The term "treating" or "treatment" herein may refer to one or more of the following: reduction of ROS levels, increasing cell viability and survival, prevention or inhibition of cell death, delaying the onset of the disease, and/or symptoms thereof, prevention, inhibition or slowing down of cell function deterioration, promotion of normal neurite growth and inhibition of abnormal neurite fasciculation. The treatment may be undertaken when a neuro-pathological condition initially develops, or may be a continuous administration, for example by administration more than once per day, every 1 day to 7 days, every 7 day to 15 days, every 15 day to 30 days, every month to two months, every two months to 6 months, or even more, to achieve the above-listed therapeutic effects.

The term "therapeutic" is intended to mean that which will elicit the biological or medical response of a tissue, a system, animal or human that is being sought by a researcher, veterinarian, medical doctor or other clinician. Similarly, administration of a "therapeutically effective amount" of a BRM or an extract obtainable from passion fruits, will achieve the goals listed above for treatment.

The term "amelioration" as referred to herein, relates to the easing, reduction, lessening or elimination of symptoms and/or causative agents of a neuro-pathological condition a subject suffers from. More specifically, "amelioration" relates to an improvement in the viability and survival of neural cells in the subject, and inhibition of their damage, death and/or deterioration of function. For instance, as a non-limiting example, the symptoms of a subject suffering from Parkinson's disease may be alleviated by inhibiting the infliction of damage to the substantia nigra, preventing further neural cell death and promoting neurite growth.

The expression "delaying the onset" means herein the postponement or slowing down of a process which inflicts damage to neural cells, inhibits their normal functions, or causes their death. Thus, the term may be understood as the protection of neural cells against the neuro-pathological disease up to a later point in time, or the postponement of the symptomatic phase of the disease.

Neural cell damage and deterioration of neural cell function may, for example, manifest in abnormal nerve fasiculation and neurite growth. Indeed, in particular embodiments, the method for the treatment, prophylaxis, amelioration, inhibition or delaying the onset of a neuro-pathological condition is effective in such cases wherein the neuro-pathological condition is characterized by damage or deterioration of function of neurons or of abnormal neurite outgrowth and fasiculation of nerves.

It should be noted that by using the term "characterized by" the invention further encompasses any condition characterized by, associated, linked to or connected with said neural cell damage. It is understood that the interchangeably used terms "associated", linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology.

In one embodiment, the condition treated by the method of the invention may be a condition characterized by abnormal neurite outgrowth and fasiculation of nerves. The term "fasiculation" relates to is a small, local, involuntary muscle contraction and relaxation visible under the skin arising from the spontaneous discharge of a bundle of skeletal muscle fibers (muscle fascicle) activated by a bundle of motor neurons, and the expression "abnormal neurite fasiculation of nerves" relates to nerve fasculation instigated by pathological conditions, such as: neuromyotonia/Isaacs syndrome, lower motor neuron lesion, Werdnig-Hoffman disease, amyotrophic lateral sclerosis, Kennedy disease, organophosphate poisoning, benzodiazepine withdrawal, magnesium deficiency, myalgic encephalomyelitis, dehydration, fatigue, lyme disease, myasthenia gravis, rabies and fibromyalgia.

The term "neurite" refers to any projection from the cell body of a neuron. This projection can be either an axon or a dendrite. The term is frequently used when speaking of immature or developing neurons, especially of cells in culture, because it can be difficult to tell axons from dendrites before differentiation is complete.

The expression "abnormal neurite growth" relates to the absence of such projection from the cell body of a neuron, the inhibition or delay of its growth, to its deformation, to the abnormal gene expression patterns therein, to abnormal metabolic processes therein, and to any other defect in its development as compared to normal, healthy neurons.

As disclosed here, the inventors found that cultivars 428 and PD, and especially cultivar 428, are effective in the treatment of the above-described disorders.

In line with these discoveries, according to some embodiments of the methods of treatment of the invention, the passion fruits used for obtaining the BRM or extract, are of at least one of a cultivar designated 428 and a cultivar designated PD, or any crosses or progeny thereof.

In a more specific embodiment, the passion fruits are of a cultivar designated 428, or any crosses or progeny thereof.

According to some embodiments of the method of treatment of the invention, the BRM or an extract obtainable from passion fruits is any one of a juice, fruit skin, pulp or seeds obtained from at least one variety or cultivar of passion fruits, or a mixture of two or more cultivars of passion fruits, or any concentrate or preparation obtained from the juice, fruit skin, pulp, seeds or fruits.

As shown in Examples 2-4 and FIGS. 3A-3C, 4A-4B and 5A-5B, the extract of passion fruits is effective in protecting neuronal cells from cell damage, and death by increasing survival and reducing cellular ROS levels. Accordingly, in particular embodiments of the method of treatment of the invention, the extract of passion fruits reduces at least one of radical cellular oxygen species (ROS) levels, oxygen species toxicity and glutamate toxicity.

According to one embodiment, the method of the invention may be particularly useful in treating neuro-pathological conditions. In one embodiment, such neuro-pathological condition may be a neurodegenerative disorder, a condition involving neurological injury or an ischemic disease or condition.

Neurodegeneration is the umbrella term for the progressive loss of structure or function of neurons, including death of neurons. Many neurodegenerative diseases including Parkinson's, Alzheimer's, ALS and Huntington's occur as a result of neurodegenerative processes. Other examples of neurodegenerative include Friedreich's ataxia, Lewy body disease, spinal muscular atrophy, multiple sclerosis, frontotemporal dementia, corticobasal degeneration, progressive supranuclear palsy, multiple system atrophy, hereditary spastic paraparesis, amyloidoses and Charcot Marie Tooth. It should not be overlooked that normal aging processes include progressive neurodegeneration.

It is appreciated that the invention is also applicable to neurodegenerative disorders that are metabolic (diabetes) related, and toxin-induced.

In yet another embodiment, the method of the invention may be applicable in treating condition involving neurological injury. The term "condition involving neurological injury" refers to traumatic head or brain injury (including epilepsy), spinal cord injury, peripheral nerve injury or peripheral neural cell injury.

Still further, the method of the invention may be used for treating ischemic disease or condition. The term "ischemic disease or condition" relates to cerebrovascular disorders, non-limiting examples of which include subarachnoid hemorrhage, intracerebral hemorrhage, occlusion and stenosis of precerebral arteries, occlusion and stenosis of basilar artery, occlusion and stenosis of carotid artery, occlusion and stenosis of vertebral artery, occlusion of cerebral arteries, cerebral thrombosis with or without cerebral infarction, cerebral embolism with or without cerebral infarction, transient cerebral ischemia, basilar artery syndrome, vertebral artery syndrome, subclavian steal syndrome, vertebrobasilar artery syndrome, transient ischemic attack (TIA), cerebral atherosclerosis, hypertensive encephalopathy, cerebral aneurysm, cerebral arteritis, Moyamoya Disease, nonpyogenic thrombosis of intracranial venous sinus, atherosclerosis, atherosclerosis of renal artery, atherosclerosis of native arteries of the extremities, intermittent claudication, aortic aneurysm, dissection of aorta, dissection of carotid artery, dissection of iliac artery, dissection of renal artery, dissection of vertebral artery, erythromelalgia, and polyarteritis nodosa and allied conditions.

According to one specific embodiment, the method of the invention is intended for treating a neurodegenerative disorder. In a more specific embodiment, the neurodegenerative disorder may be any one of Parkinson's disease, Alzheimer's disease or ALS. In a particular embodiment, the neurodegenerative disorder is aging-related neurodegeneration.

Parkinson's disease is a complex neurodegenerative disorder involving the predominant loss of dopaminergic neurons in the substantia nigra pars compacta (SNc), subsequent decay of the nigrostriatal tract and associated movement anomalies such as rigidity, bradykinesia and tremor. The foremost pathological features associated with SNc degeneration are mitochondrial abnormalities, ergogenic failure, excessive dopamine (DA) oxidation, Lewy body deposition, a-synuclein/ubiquinated protein aggregation, heightened concentration of redox-active free iron and a gradual loss of neuromelanin in and around the SNc. Further, the extensive loss of endogenous antioxidant enzyme systems and reduced glutathione (GSH) can render even high levels of oxidative stress and associated lipid/protein nitration (via ONOO—)/oxidation (via $O_2$, $H_2O_2$ and OH). These events are clearly evidenced by the accumulation of 3-nitrotyrosine, protein carbonyls, 8-hydroxyguanosine, malondialdehyde and hydroxynonenol in the SNc area. In addition, subsequent chronic inflammation further aggravates the problem involving microglial activation, astrogliosis, release of cytotoxic molecules, free radicals and glutamate, all of which can further conspire excitotoxic, apoptotic and necrotic neurodegenerative cell death. Susceptibility of these events to occur in the SNc of any one particular individual could be dependent upon a number of factors including: hereditary genetic mutations (i.e. parkin, DJ-1, PINK-I, LRRK2, park-1, ubiquitin-carboxy-terminal-hydrolase LI), defects in mitochondrial function, exposure to environmental mitochondrial toxins, head trauma, viral/bacterial infections, metals, antipsychotic/antidepressant drugs or rural/farm living.

To date, the standard medical treatment for Parkinson's disease involves the use of therapeutics that mitigate neurological effects through modulation/regulation of neurotransmitter function (i.e. levodopa/dopa-decarboxylase inhibitors Sinemet® and Madopar®, dopamine agonists, catechol-o-methyltransferase inhibitors, monoamine oxidase (MAO) inhibitors, anti-cholinergics and surgical treatments).

Alzheimer's disease is characterised by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

In yet another embodiment, the method of the invention may be used for treating Alzheimer's disease. Alzheimer's disease has been identified as a protein misfolding disease (proteopathy), caused by accumulation of abnormally folded A-beta and tau proteins in the brain. Plaques are made up of small peptides, 39-43 amino acids in length, called beta-amyloid (also written as A-beta or Aβ). Beta-amyloid is a fragment from a larger protein called amyloid precursor protein (APP), a transmembrane protein that penetrates through the neuron's membrane. APP is critical to neuron growth, survival and post-injury repair. In Alzheimer's disease, an unknown process causes APP to be divided into smaller fragments by enzymes through proteolysis. One of these fragments gives rise to fibrils of beta-amyloid, which form clumps that deposit outside neurons in dense formations known as senile plaques.

Still further, in certain embodiments, the method of the invention may be used for treating ALS. Amyotrophic lateral sclerosis (abbreviated ALS, also referred to as Lou Gehrig's disease) is a form of motor neuron disease caused by the degeneration of neurons located in the ventral horn of the spinal cord and the cortical neurons that provide their afferent input. The disorder is characterized by rapidly progressive weakness, muscle atrophy and fasciculations, spasticity, dysarthria, dysphagia, and respiratory compromise. Sensory function generally is spared, as is autonomic, and oculomotor activity. ALS is a progressive, fatal, neurodegenerative disease with most affected patients dying of respiratory compromise and pneumonia after 2 to 3 years; although occasional individuals have a more indolent course and survive for many years.

Another embodiment of the invention provides a method for treating HD. Huntington's disease (HD) causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder.

Mutant Huntingtin is an aggregate-prone protein. During the cells' natural clearance process, these proteins are retrogradely transported to the cell body for destruction by lysosomes. It is a possibility that these mutant protein aggregates damage the retrograde transport of important cargoes such as BDNF by damaging molecular motors as well as microtubules.

The greatest risk factor for neurodegenerative diseases is aging. Mitochondrial DNA mutations as well as oxidative stress both contribute to aging. Many of these diseases are late-onset, meaning there is some factor that changes as a person ages for each disease. One constant factor is that in each disease, neurons gradually lose function as the disease progresses with age. Therefore, according to certain embodiments, the methods of the invention are applicable for treating ischemic disease or condition. In a more specific embodiment, the ischemic disease or condition is stroke.

A stroke, previously known medically as a cerebrovascular accident (CVA), is the rapidly developing loss of brain function(s) due to disturbance in the blood supply to the brain. This can be due to ischemia (lack of blood flow) caused by blockage (thrombosis, arterial embolism), or a hemorrhage (leakage of blood). As a result, the affected area of the brain is unable to function, which might result in an inability to move one or more limbs on one side of the body, inability to understand or formulate speech, or an inability to see one side of the visual field. A stroke is a medical emergency and can cause permanent neurological damage, complications, and death. It is the leading cause of adult disability in the United States and Europe and the second leading cause of death worldwide. Risk factors for stroke include old age, hypertension (high blood pressure), previous stroke or transient ischemic attack (TIA), diabetes, high cholesterol, cigarette smoking and atrial fibrillation. High blood pressure is the most important modifiable risk factor of stroke.

In yet another embodiment, the method of the invention may be used for treating a condition involving neuronal injury. In another specific embodiment, the condition involving neurological injury may be any one of acute, traumatic or chronic brain injury.

An acute brain injury or traumatic brain injury (TBI) is a nondegenerative, noncongenital insult to the brain from an external mechanical force, possibly leading to permanent or temporary impairment of cognitive, physical, and psychosocial functions, with an associated diminished or altered state of consciousness. The definition of TBI has not been consistent and tends to vary according to specialties and circumstances. Often, the term brain injury is used synonymously with head injury, which may not be associated with neurologic deficits. The definition also has been problematic with variations in inclusion criteria.

TBI can be classified based on severity, mechanism (closed or penetrating head injury), or other features (e.g. occurring in a specific location or over a widespread area). Head injury usually refers to TBI, but is a broader category because it can involve damage to structures other than the brain, such as the scalp and skull. Brain trauma can be caused by a direct impact or by acceleration alone. In addition to the damage caused at the moment of injury, brain trauma causes secondary injury, a variety of events that take place in the minutes and days following the injury. These processes, which include alterations in cerebral blood flow and the pressure within the skull, contribute substantially to the damage from the initial injury. TBI can cause a host of physical, cognitive, emotional, and behavioral effects, and outcome can range from complete recovery to permanent disability or death.

Glutamate levels, increased clinically after TBI, may affect other paths related to secondary head injury including the initiation of apoptosis by activation of NMDA-R, calcium dependent production of nitric oxide and development of super oxides and free radical damage to DNA and cellular membranes. Intact blood brain barrier (BBB) after TBI or stroke may contribute to accumulation of glutamate and is assumed to have a deleterious effect on brain function.

In yet another embodiment, the invention may be applicable for treating chronic brain injuries. Chronic brain injuries are defined as conditions characterized by persistent brain damage or dysfunction as sequelae of cranial trauma. This disorder may result from diffuse axonal injury; intracranial hemorrhages; brain edema; and other conditions. Clinical features may include dementia; focal neurologic deficits; persistent vegetative state; akinetic mutism; or coma. Chronic brain injury is sometimes referred to as post-traumatic, chronic encephalopathy, post-concussive chronic encephalopathy, chronic traumatic encephalopathy, chronic post-traumatic encephalopathy, chronic post-concussive syndrome, chronic post-concussive encephalopathy, brain, chronic injury and post-concussive syndrome.

A major advantage of the methods and compositions of the invention is the readily-available and easy to process or manipulate active substance, i.e., the *Passiflora* fruit. This ease permits the administration or use of the substance in a variety of modes. More specifically, it is understood that according to certain embodiments, the BRM or extract of passion fruits used by the methods of the invention may be administered as part of a nutraceutical composition, pharmaceutical composition, functional food, functional nutrition product, medical food, medical nutrition product, or dietary supplement.

In one specific embodiment, the BRM or extract of the invention may be administered as part of a nutraceutical composition.

In another specific embodiment, the BRM or extract of the invention may be administered as part of a functional food.

In another specific embodiment, the BRM or extract of the invention may be administered as part of a medical food.

The terms "nutraceutical" combines the words "nutrition" and "pharmaceutical". It is a food or food product that provides health and medical benefits, including the prevention and treatment of disease. A nutraceutical is a product isolated or purified from foods that is generally sold in medicinal forms not usually associated with food. A nutraceutical is demonstrated to have a physiological benefit or provide protection against chronic disease. Such products may range from isolated nutrients, dietary supplements and specific diets to genetically engineered foods, herbal products, and processed foods such as cereals, soups, and beverages. Nutraceutical foods are not subject to the same testing and regulations as pharmaceutical drugs.

The term "nutraceutical" as used herein denotes usefulness in both nutritional and pharmaceutical fields of application. Thus, novel nutraceutical compositions can be used as supplements to food and beverages and as pharmaceutical formulations for enteral or parenteral application which may be solid formulations, such as capsules or tablets, or liquid formulations, such as solutions or suspensions.

The nutraceutical compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, jellifying agents, gel-forming agents, antioxidants and antimicrobials.

Moreover, a multi-vitamin and mineral supplement may be added to nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The nutraceutical compositions according to the present invention may be in any galenic form that is suitable for administering to the body, especially in any form that is conventional for oral administration, e.g. in solid forms such as (additives/supplements for) food or feed, food or feed premix, fortified food or feed, tablets, pills, granules, dragees, capsules and effervescent formulations, such as powders and tablets, or in liquid forms, such as solutions, emulsions or suspensions as e.g. beverages, pastes and oily suspensions. The pastes may be incorporated in hard or soft shell capsules, whereby the capsules feature e.g. a matrix of (fish, swine, poultry, cow) gelatine, plant proteins or ligninsulfonate. Examples for other application forms are those for transdermal, parenteral or injectable administration. The dietary and pharmaceutical compositions may be in the form of controlled (delayed) release formulations.

Beverages encompass non-alcoholic and alcoholic drinks as well as liquid preparations to be added to drinking water and liquid food. Non-alcoholic drinks are e.g. soft drinks, sports drinks, fruit juices, teas and milk-based drinks. Liquid foods are e.g. soups and dairy products. The nutraceutical composition containing *Passiflora* BRM or extract may be added to a soft drink, an energy bar, or a candy.

If the nutraceutical composition is a pharmaceutical formulation the composition further contains pharmaceutically acceptable excipients, diluents or adjuvants. Standard techniques may be used for their formulation, as e.g. disclosed in Remington's Pharmaceutical Sciences, 20th edition Williams & Wilkins, PA, USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

In one specific embodiment, the BRM or extract used by the method of the invention may be administered as part of a functional food.

"Functional food", "functional nutrition product", "medical food" and "medical nutrition product" relate to any healthy food claimed to have a health-promoting or disease-preventing property beyond the basic function of supplying nutrients. The general category of functional foods includes processed food or foods fortified with health-promoting additives, like "vitamin-enriched" products.

A dietary supplement, also known as food supplement or nutritional supplement, is a preparation intended to supplement the diet and provide nutrients, such as vitamins, minerals, fiber, fatty acids, or amino acids, that may be missing or may not be consumed in sufficient quantities in a person's diet. Some countries define dietary supplements as foods, while in others they are defined as drugs or natural health products. Supplements containing vitamins or dietary minerals are included as a category of food in the Codex Alimentarius, a collection of internationally recognized standards, codes of practice, guidelines and other recommendations relating to foods, food production and food safety. These texts are drawn up by the Codex Alimentarius Commission, an organization that is sponsored by the Food and Agriculture Organization of the United Nations (FAO) and the World Health Organization (WHO).

In addition to providing a method of using BRM or *Passiflora* extracts, the inventors also disclose the corresponding uses of these novel active ingredients. Thus, in the fourth aspect, the invention provides a botanical raw material (BRM) or an extract obtainable from passion fruits for use in the treatment, prophylaxis, amelioration, inhibition or delaying the onset of a neuro-pathological condition.

In particular embodiments, the BRM or extracts of passion fruit may be used for treating a neuro-pathological condition characterized by damage or deterioration of function of neurons or of promotion of neurite outgrowth and fasiculation of nerves.

The invention contemplates more specific embodiments, where the BRM or extract according to the invention were obtained from passion fruits of a cultivar designated 428 and a cultivar designated PD, or any crosses or progeny thereof.

In yet more specific embodiments of the BRM or extract of the invention, the passion fruits are of a cultivar designated 428, or any crosses or progeny thereof.

It is appreciated that the BRM or extract of passion fruits (or botanical raw material (BRM), botanical drug substance (BDS), purified BDS or an extract obtainable from passion fruits) according to the invention, may be any one of a juice, fruit skin, pulp or seeds obtained from at least one variety or cultivar of passion fruits or a mixture of two or more cultivars of passion fruits, or any fraction, concentrate or preparation obtained from the juice, fruit skin, pulp, seeds or whole fruits. The nature of the cultivar mixtures according to the invention is discussed above.

It should be noted that botanical substances which are derived from *Passiflora* fruits include primary extracts prepared by processes such as for example, crude water-based extraction, filtering and centrifugation.

In numerous embodiments, the BRM or extract of the invention may be used for protection from, reduction, prevention or inhibition of neural cell damage or deterioration in neural cell function.

The BRM or extract used by the invention may reduce at least one of radical cellular oxygen species levels, oxygen species toxicity and glutamate toxicity.

Some embodiments contemplate the BRM or extract of passion fruit according to the invention, for use in treating a neuro-pathological condition. In specific embodiments, the neuro-pathological condition may be a neurodegenerative disorder, a condition involving neurological injury or an ischemic disease or condition.

According to certain embodiments, the BRM or extract of the invention may be used for treating a neurodegenerative disorder such as Parkinson's disease, Alzheimer's disease or ALS.

In one embodiment, the BRM or extract of the invention may be used for treating an ischemic disease or condition, for example, stroke.

In another embodiment, the BRM or extract of the invention may be used for treating a condition involving neurological injury. More specifically, such condition may be any one of acute, traumatic or chronic brain injury.

In certain embodiments, the BRM or extract of the invention may be administered as part of a nutraceutical composition, pharmaceutical composition, functional food, functional nutrition product, medical food, medical nutrition product, dietary supplement or botanical drug.

In yet another embodiment, the BRM or extract of the invention may be administered as part of a functional food.

In a further aspect, the invention is directed to the use of a botanical raw material (BRM) or an extract obtainable from passion fruits in the preparation of a composition for the treatment, prophylaxis, amelioration, inhibition or delaying the onset of a neuro-pathological condition.

According to more specific embodiments of the use of the invention, the passion fruits are of at least one of a cultivar designated 428 and a cultivar designated PD, or any crosses or progeny thereof.

In yet more specific embodiments of the use of the invention, the passion fruits are of a cultivar designated 428, or any crosses or progeny thereof.

Furthermore, according to other embodiments of the use of the invention, the BRM or extract of passion fruits according to the invention may be any one of a juice, fruit skin, pulp or seeds obtained from at least one variety or cultivar of passion fruits or a mixture of two or more cultivars of passion fruits, or any fraction, concentrate or preparation obtained from the juice, fruit skin, pulp, seeds or whole fruits. The nature of the cultivar mixtures according to the invention is discussed above.

In numerous embodiments of the use of the invention, the prepared composition is for protection from, reduction, prevention or inhibition of neural cell damage or deterioration in neural cell function.

The composition prepared according to the use of the invention may reduce at least one of radical cellular oxygen species levels, oxygen species toxicity and glutamate toxicity.

Furthermore, according to particular embodiments, the composition prepared by the use of the invention is effective in the treatment of a neuro-pathological condition, wherein the neuro-pathological condition is a neurodegenerative disorder, a condition involving neurological injury or an ischemic disease or condition.

According to other embodiments of the use of the invention, the neuro-pathological condition is any one of Parkinson's disease, Alzheimer's disease or ALS.

In one embodiment of the use of the invention, the ischemic disease or condition is stroke.

In another embodiment of the use of the invention, the condition involving neurological injury is any one of acute, traumatic or chronic brain injury.

In certain embodiments of the use of the invention, the BRM or extract of passion fruits is administered as part of a nutraceutical composition, pharmaceutical composition, functional food, functional nutrition product, medical food, medical nutrition product, dietary supplement or botanical drug.

In some embodiments of the use of the invention, it is administered as part of a functional food.

In another aspect, the invention relates to a composition for protection from, reduction, prevention or inhibition of neural cell damage or deterioration in neural cell function. More specifically, the composition of the invention may comprise a BRM or an extract of passion fruits. The composition optionally further comprises a pharmaceutically acceptable carrier, excipient or diluent.

In a further aspect, the invention is directed to a composition for the treatment, prophylaxis, amelioration, inhibition or delaying the onset of a neuro-pathological condition in a subject. The composition comprises as an active ingredient a botanical raw material (BRM) or an extract of passion fruits.

It should be appreciated that the passion fruits extract or BRM comprised in the compositions according to the invention may be obtained from passion fruits of at least one of a cultivar designated 428 and a cultivar designated PD or of any crosses or progeny thereof.

More specifically, the invention provides compositions comprising BRM or extracts obtained from passion fruits of a cultivar designated 428, or of any crosses or progeny thereof.

According to certain embodiments, the BRM or extract comprised in the compositions of the invention may be any one of a juice, fruit skin, pulp or seeds obtained from at least one variety or cultivar of passion fruits or a mixture of two or more cultivars of passion fruits, or any concentrate or preparation obtained from the juice, fruit skin, pulp, seeds or whole fruits.

According to certain embodiments, the compositions of the invention are suitable for protection from, reduction, prevention or inhibition of neural cell damage or deterioration in neural cell function.

In some embodiments, the BRM or extract of passion fruits comprised in said compositions reduces at least one of radical cellular oxygen species (ROS) levels, oxygen species toxicity and glutamate toxicity.

In other embodiments, the composition according to the invention may be applicable for treating a neuro-pathological condition, for example, e a neurodegenerative disorder, a condition involving neurological injury or an ischemic disease or condition.

In one specific embodiment, the composition of the invention is intended for treating a neurodegenerative disorder. Such disorder may be any one of Parkinson's disease, Alzheimer's disease or ALS.

In another embodiment, the composition of the invention may be used for treating an ischemic disease or condition, for example, stroke.

In yet another embodiment, the composition of the invention may be used for treating a condition involving neurological injury, specifically, acute, traumatic or chronic brain injury.

It is understood that according to various embodiments, the composition according the invention may be a nutraceutical composition, pharmaceutical composition, functional food, functional nutrition product, medical food, medical nutrition product or dietary supplement.

It is appreciated that the composition of the invention may be any one of a pharmaceutical composition, nutraceutical composition, nutraceutical composition, functional food, functional nutrition product, medical food, medical nutrition product or dietary supplement.

In one specific embodiment, the composition of the invention may be a pharmaceutical composition. A "pharmaceutical composition" refers to a preparation of one or more of the BRM or extract of passion fruit according to the invention with other chemical components such as physiologically suitable carriers and excipients. The purpose of a pharmaceutical composition is to facilitate administration of a compound to an organism.

Still further, in certain embodiments, the composition optionally further comprises a pharmaceutically acceptable carrier, excipient or diluent. Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The term "diluent" refers to an inactive ingredient that is added to the composition in addition to the active substance or material. A diluent may be used as binders, disintegrants (help the tablet break apart in the digestive system), or flavor enhancers. In one embodiment, a diluent is solid, such as starch, cellulose derivatives, and magnesium stearate. In another embodiment, a diluent is liquid, such as water, saline, and a dextrose solution (e.g., 5%).

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Each carrier should be both pharmaceutically and physiologically acceptable in the sense of being compatible with the other ingredients and not injurious to the patient.

The pharmaceutical composition of the invention can be administered and dosed by the methods of the invention, in accordance with good medical practice, systemically, for example intravenous (i.v.), per os or intranasally. Other contemplated systemic administration routes include parenteral, e.g. intraperitoneal or intramuscular injection. In another example, the pharmaceutical composition can be introduced to a site by any suitable route including intravenous, subcutaneous, transcutaneous, topical, intramuscular, intraarticular, subconjunctival, or mucosal, e.g. oral, intranasal, or intraocular administration.

If local administration to the area in need of treatment is required, it may be achieved, for example, by local infusion during surgery, topical application, direct injection into the specific organ, etc.

Pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carriers) or excipient(s). In general formulations are prepared by uniformly and intimately bringing into association the active ingredients with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

Compositions and formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using excipients such as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

Pharmaceutical compositions used to treat subjects in need thereof according to the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

In various embodiments, the final solution may be adjusted to have a pH between about 4 and about 9, between about 5 and about 7, between about 5.5 and about 6.5, or about 6. The pH of the composition may be adjusted with a pharmacologically acceptable acid, base or buffer.

In the case of sterile powders for the preparation of the sterile injectable solutions and some oral dosage forms, the preferred method of preparation are vacuum-drying and freeze drying techniques which yield a powder of the active ingredient plus any additional desired ingredient from a previously sterile-filtered solution thereof.

For administration by nasal inhalation, the compositions comprising BRM or extract of passion fruits according to the present invention may conveniently be delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient. According to some embodiments, the compositions comprising BRM or extract of passion fruits according to the invention can be applied to a subject in need as nasal drops, ophthalmic gel, ophthalmic ointment, spray or patches.

In a further aspect, the invention provides a nutraceutical composition comprising as an active ingredient a botanical raw material (BRM) or an extract obtainable from passion fruits.

The term nutraceutical composition as used herein include food product, foodstuff, dietary supplement, nutritional supplement or a supplement composition for a food product or a foodstuff. Thus, in another embodiment the present invention relates to a nutraceutical wherein the nutraceutical is a food product, foodstuff, dietary supplement, nutritional supplement or a supplement composition for a food product or a foodstuff.

As used herein, the term food product refers to any food or feed suitable for consumption by humans or animals. The food product may be a prepared and packaged food (e.g., mayonnaise, salad dressing, bread, or cheese) or an animal feed (e.g., extruded and pelleted animal feed, coarse mixed feed or pet food composition). As used herein, the term foodstuff refers to any substance fit for human or animal consumption. Food products or foodstuffs are for example beverages such as non-alcoholic and alcoholic drinks as well as liquid preparation to be added to drinking water and liquid food, non-alcoholic drinks are for instance soft drinks, sport drinks, fruit juices, specifically, passion fruit juice, teas, near-water drinks, milk, milk replacements, and other dairy drinks such as for example yoghurt drinks, and diet drinks. In another embodiment food products or foodstuffs refer to solid or semi-solid foods comprising the composition according to the invention. These forms can include, but are not limited to baked goods such as bars, cakes, cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yoghurt and any other fat or oil containing foods, and food ingredients (e.g., wheat flour). The term food products or foodstuffs also includes functional foods and prepared food products, the latter referring to any pre-packaged food approved for human consumption.

In one embodiment, the nutraceutical composition of the invention comprises BRM or extracts obtained from passion of at least one of a cultivar designated 428 and a cultivar designated PD, or any crosses and progeny thereof.

In a specific embodiment, the nutraceutical composition of the invention comprises BRM or extract obtained from passion fruits of a cultivar designated 428, or any crosses and progeny thereof.

In certain embodiments, the BRM or extract of the nutraceutical composition of the invention, may be any one of a juice, fruit skin, pulp or seeds obtained from at least one variety or cultivar of passion fruits or a mixture of two or more cultivars of passion fruits, or any concentrate or preparation obtained from the juice, pulp, seed fruit skin or whole fruits.

In other embodiments, the nutraceutical composition of the invention is for protection from, reduction, prevention or inhibition of neural cell damage or deterioration in neural cell function.

According to particular embodiments, the nutraceutical composition of the invention reduces at least one of radical cellular oxygen species (ROS) levels, oxygen species toxicity and glutamate toxicity.

According to yet further embodiments, the nutraceutical composition of the invention may be applicable for treating a neuro-pathological condition, for example, a neurodegenerative disorder, a condition involving neurological injury or an ischemic disease or condition.

In more specific embodiment, the nutraceutical composition of the invention may be used for treating a neurodegenerative disorder such as Parkinson's disease, Alzheimer's disease or ALS.

According to other embodiments, the nutraceutical composition of the invention may be used for ischemic disease or condition, for example, stroke.

In alternative embodiments, the nutraceutical composition of the invention may be used for treating conditions involving neurological injury, specifically, acute, traumatic or chronic brain injury.

In yet another aspect, the invention is directed to a functional food comprising as an active ingredient a botanical raw material (BRM) or an extract obtainable from passion fruits.

"Functional food", "Functional food products", according to the present invention is defined as food product (including beverages) suitable for human consumption. The expression comprises any fresh or processed food having a health-promoting and/or disease-preventing property beyond the basic nutritional function of supplying nutrients, including food made from functional food ingredients or fortified with health-promoting additives, especially with an effects in the prophylaxis or treatment of one or more of the disorders mentioned herein, especially allowing for neuro-protection which a BRM or extract obtainable from passion fruit according to the invention is added as an ingredient (especially additive) as health benefit agent, especially in an effective amount, as well as any partially or totally artificially composed food. The term "food" as used herein refers to (1) articles used for food or drink for man or other animals; (2) chewing gum; and (3) articles used for components of any such article. The term "Functional food" or "functional nutrition product" refers to a food or nutrition product that is sold (e.g. in a supermarket or online) without any restrictions.

In one embodiment, the functional food of the invention comprises BRM or extracts obtained from passion fruits of at least one of a cultivar designated 428 and a cultivar designated PD, or any crosses or progeny thereof.

In a specific embodiment, the functional food of the invention comprises BRM or extracts obtained from passion fruits of a cultivar designated 428, or any crosses or progeny thereof.

In certain embodiments, the BRM or extract comprised in the functional food of the invention may be any one of a juice, fruit skin, pulp or seeds obtained from at least one variety or cultivar of passion fruits or a mixture of two or more cultivars of passion fruits, or any concentrate or preparation obtained from the juice, fruit skin, pulp or seeds or fruits.

In other embodiments of the functional food of the invention, the nutraceutical is for protection from, reduction, prevention or inhibition of neural cell damage or deterioration in neural cell function.

According to particular embodiments, the functional food of the invention reduces at least one of radical cellular oxygen species (ROS) levels, oxygen species toxicity and glutamate toxicity.

According to yet further embodiments, the functional food of the invention is intended for treating a neuropathological condition, for example, a neurodegenerative disorder, a condition involving neurological injury or an ischemic disease or condition.

In more specific embodiment, the functional food of the invention may be used for treating a neurodegenerative disorder, specifically, any one of Parkinson's disease, Alzheimer's disease or ALS.

According to other embodiments, the functional food of the invention may be used in cases of ischemic disease or condition, specifically, in cases of stroke.

In alternative embodiments, the functional food of the invention may be used for condition involving neurological injury, for example, any one of acute, traumatic or chronic brain injury.

In another aspect, the invention is directed to a medical food comprising as an active ingredient a botanical raw material (BRM) or an extract obtainable from passion fruits. The term "medical food" or "medical nutrition product" refers to a food or nutrition product with is prescribed by a physician. Foods or nutrition products may be solids, liquids, gels, powders or gases. Examples of solids are fruit-based drinks, coffee-based drinks, tea-based drinks, sport drinks, nutrition bars, snack foods, gums, cereals, candies, baby formulas, energy drinks, adult nutritional drinks, health drinks, and other food products.

In one embodiment, the medical food of the invention comprises BRM or extracts obtained from passion fruits of at least one of a cultivar designated 428 and a cultivar designated PD, or any crosses or progeny thereof.

In a specific embodiment, the medical food of the invention comprises BRM or extracts obtained from passion fruits of a cultivar designated 428, or any crosses or progeny thereof.

In certain embodiments, the BRM or extract comprised in the medical food of the invention may be any one of a juice, fruit skin, pulp or seeds obtained from at least one variety or cultivar of passion fruits or a mixture of two or more cultivars of passion fruits, or any concentrate or preparation obtained from the juice, fruit skin, pulp or seeds or fruits.

In other embodiments of the medical food of the invention, the nutraceutical is for protection from, reduction, prevention or inhibition of neural cell damage or deterioration in neural cell function.

According to particular embodiments, the medical food of the invention reduces at least one of radical cellular oxygen species (ROS) levels, oxygen species toxicity and glutamate toxicity.

According to yet further embodiments, the medical food of the invention is intended for treating a neuro-pathological condition, for example, a neurodegenerative disorder, a condition involving neurological injury or an ischemic disease or condition.

In more specific embodiment, the medical food of the invention may be used for treating a neurodegenerative disorder, specifically, any one of Parkinson's disease, Alzheimer's disease or ALS.

According to other embodiments, the medical food of the invention may be used in cases of ischemic disease or condition, specifically, in cases of stroke.

In alternative embodiments, the medical food of the invention may be used for condition involving neurological injury, for example, any one of acute, traumatic or chronic brain injury.

It should be appreciated that the BRM or extract of the invention or any or composition containing the same, can be used alone or in combination with another therapeutic agent to treat diseases. It should be understood that the passion fruits BRM or extract of the invention can be used alone or in combination with an additional agent, e.g., a therapeutic agent, said additional agent being selected by the skilled artisan for its intended purpose. For example, the additional agent can be a therapeutic agent that is art-recognized as being useful to treat the disease or condition being treated by the present invention. The additional agent also can be an agent that imparts a beneficial attribute to the therapeutic composition e.g., an agent that affects the viscosity of the composition.

The combination therapy contemplated by the invention includes, for example, administration of the BRM or extract of the invention, and additional agent(s) in a single pharmaceutical formulation as well as administration of the BRM or extract of the invention, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

It should further be understood that the combinations included within the invention are those combinations useful for their intended purpose. The combination can also include more than one additional agent, e.g., two or three additional agents if the combination is such that the formed composition can perform its intended function. In some embodiments, the additional agent could be another BRM or extract of the invention.

More specifically, it is well-known that N-acetyl-cysteine (NAC) promotes cellular glutathione production, and thus reduces, or even prevents, oxidant mediated damage. Treatment with NAC provides beneficial effects in a number of respiratory, cardiovascular, endocrine, infectious, and other disease settings.

B vitamins, such as folic acid, are known to reduce levels of homocysteine, an amino acid already linked, at high levels, to an increased risk of heart attacks, strokes and Alzheimer's disease.

Lecithin, a lipid material composed of choline and inositol, is a major component of cell membranes. As used by producers of lecithin for commercial use, the term "lecithin" refers to a complex mix of phosphatides and other substances that contain phosphatidylcholine.

Choline (trimethyl ethanolamine), a quaternary saturated amine classified as an essential nutrient by the Food and Nutrition Board of the Institute of Medicine, is a component of lecithin. Choline is needed by the body to make the neurotransmitter acetylcholine.

Omega-3 fatty acids are a family of unsaturated fatty acids that have in common a final carbon-carbon double bond in the n−3 position; that is, the third bond from the methyl end of the fatty acid. Nutritionally important n−3 fatty acids include α-linolenic acid (ALA), eicosapentaenoic acid (EPA), and docosahexaenoic acid (DHA), all of which are polyunsaturated. Some experts believe these compounds can help regulate cholesterol in the body. They may also help protect the brain from cognitive problems associated with Alzheimer's disease.

Still further, it should be noted that the invention also provides kits for conveniently and effectively implementing the methods of this invention. Such kits comprise any subject compound, composition and/or extract, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

For example, the present invention also provides for kits containing at least one dose of a subject BRM or extract of passion fruit, and often many doses, and other materials for a treatment regimen. For example, in one embodiment, a kit of the present invention contains sufficient subject BRM or extract of passion fruit for from five to thirty days and optionally equipment and supplies necessary to measure one or more indices relevant to the treatment regimen. In another embodiment, kits of the present invention contain all the materials and supplies, including subject BRM or extract of passion fruit, for carrying out any methods of the present invention. In still another embodiment, kits of the present invention, as described above, additionally include instructions for the use and administration of the subject compositions.

In one embodiment, the invention is a pharmaceutical kit comprising one or more subject BRM or extract of passion fruit in an amount sufficient to enhance long-term memory in a patient, a pharmaceutically acceptable carrier, and instructions (written and/or pictorial) describing the use of the subject BRM or extract of passion fruit for neuroprotection.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." It must be noted that, as used in this specification and the appended claims, the singular forms "a", "an" and "the" include plural referents unless the content clearly dictates otherwise.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures. More specifically, the terms "comprises", "comprising", "includes", "including", "having" and their conjugates mean "including but not limited to". The term "consisting of means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley; Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998). "Nucleic Acid Hybridization" Hames, B. D., and Higgins S. J., eds. (1985); "Transcription and Translation" Hames, B. D., and Higgins S. J., Eds. (1984); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Reagents

Dulbecco's Modified Eagles Medium (DMEM) (Invitrogen, CA, USA)
Fetal calf serum (Biological industries, Israel)
Glutamine (Biological industries, Israel)
Penicillin (Biological industries, Israel)
Streptomycin (Biological industries, Israel)
Phosphate buffered saline (PBS) (Invitrogen, CA, USA)
Trypsin×2 (Biological industries, Israel)
Glucose oxidase (Sigma-Aldrich, St. Louis, Mo., USA)
N-acetyl cysteine (NAC) (Sigma-Aldrich, St. Louis, Mo., USA)
Propidium iodide (PI) (Sigma-Aldrich, St. Louis, Mo., USA)
Toluene (Sigma-Aldrich, St Louis, Mo., USA)

Equipment

Flow cytometer (FACScalibur, BD Biosciences, San Josa, Calif., USA)
ESA Coulochem II electrochemical coulometric detector (Bedford, Mass.)
Phenomenex Synergi column (250 mm×4.6 mm×4 µm) (Torrance, Calif.)
Cryostat (Leica, Germany)
Gas Chromatograph model 7890A (Agilent, Santa Clara, Calif., USA) equipped with an HP-5 capillary column (30 m×0.25 mm i.d., 0.25 µm film thickness; Agilent), coupled to an Agilent 5975C MS detector.
UltroSpec 2100pro (Amersham Biosciences)
Abbe model 10450 (American Optical, Buffalo, N.Y.)
TIM 850 (Radiometer, Copenhagen, Denmark)

Experimental Procedures

Plant Material

*Passiflora edulis* of PD, 100, 109, 230, 428 and 440 cultivars were collected after abscising or picked (cultivar 428 was picked during winter) after achieving full size and mature color in the Faculty of Agriculture in Rehovot, Israel. To maintain consistency, fruits which abscised no longer than 24 hours were collected. The different cultivars were chosen from approximately 900 seedlings of selfed PD plants. PD anthesis occurs twice a year in Israel, and there are two yields a year, in summer and winter, thus comparisons between the cultivars were performed in both winter and summer, separately. Fruits were weighed and stored, and 4-6 fruits per cultivar were packed in 1 L containers, sealed in shrink wrap to avoid fruit skin shrinking and to simulate commercial storage conditions. The containers were kept at 12° C. for 22 days (storage period), and the fruits were then unwrapped, and transferred to 20° C. for 5 days (shelf life period).

Fruit is collected from different lines and its content is examined immediately and after storage. Extracts are taken for GCMS analysis for head space solid phase microextraction (SPME). Levels of SH containing compounds are measured as described [Tapp E. J. et al., (2008) J. Agric. Food Chem. 56:6623-6630]. Concentrations of total SH groups determined by Ellman reaction [Ellman G. L. (1959) Arch. Biochem. Bioph. 82:70-77] are measured in the extracts prior to the start of the cell culture studies, in order to define the extract composition with respect to compounds of known biological activity.

Extract Preparation

Extraction of passion fruits was performed as follows: the passion fruit pulp (including seeds) or juice was acquired by juicing the fruits and squeezing the material obtained into a gauze pad, filtering clear juice into test tubes that are then stored at −20° C. Prior to freezing or after thawing, the juice was further clarified by centrifugation at 12,000 RPM for 5 minutes and collection of the clear supernatant. If needed, extracts are concentrated by speedvac, or by freeze-drying and resolubilization.

Carotenoid Extraction

*Passiflora* Juices were collected on harvest day, after storage in refrigeration (12° C. for 22 days) and after shelf life (20° C. for 5 days). 2 ml ether petrol and 6 ml isopropanol were added to 2 ml juice. The mixture was agitated and gases were released. Following gas release, 5 ml ether and 4 ml saturated NaCl solution were added. The mixture was agitated for 10 minutes for phase separation. A 1 ml sample of the top (organic) phase, comprising carotenoids was taken for a spectrophotometric reading. Spectra between wavelengths 200 nm-600 nm were read, as the main *Passiflora* carotenoid species (beta and zeta carotene) peak at 400, 425, 450 and 480 nm [Pruthi J. S. and Lal G (1958), J. Food Sci. 23:505-510; Talcott S. T. et al., (2003) J. Agric. Food Chem. 51:935-941].

Volatile Analysis

Fresh passion fruit juice was extracted as described above. Samples were placed in 20 ml amber vials, each sample containing 1 ml juice, 1 ml of 200 g/L NaCl and additional 0.6 g NaCl. High salt concentration prevents enzymatic activity associated with volatile biosynthesis and increases volatile partitioning [Buttery, R. G. and Ling, L. C., ACS. Symp. Series (1993), 525:23-34], as was also reported in passion fruit juice [Pontes, M. et al., Microchemical J. (2009), 93 (1):1-11]. 5 µl of toluene diluted 1:1000 (v/v) were added to each vial as an internal standard. The vials were sealed with screw caps and stored at −20° C. until analysis.

Aroma volatiles were detected by gas chromatograph-mass spectrometer (GC-MS). Prior to analysis, samples were incubated for 1 hour at 30° C. to obtain equilibrium. Volatiles were then absorbed for 10 min from vial headspace by solid phase microextraction (SPME) onto a fiber (1 cm long, 100 µm thick) coated with polydimethylsiloxane (PDMS) (Sigma-Aldrich/Supelco, Bellefonte, Pa., USA). The fiber was desorbed for 5 min at 250° C. in the splitless inlet of a 7890A model GC equipped with an HP-5 capillary column (30 m×0.25 mm i.d., 0.25 µm film thickness), coupled to an Agilent 5975C MS detector. Helium was used as the carrier gas at a flow rate of 0.8 ml min$^{-1}$. The oven temperature was initially 40° C. for 1 min, ramped up to 150° C. at 10° C. min$^{-1}$ and then up to 220° C. at 15° C. min$^{-1}$ Detection was performed by the mass spectrometer in the electronic impact mode (EI at 70 eV) and mass acquisition range was 40-206 m/z; 7.72 spectra s$^{-1}$. Volatile compounds were tentatively identified by comparing their mass spectra with the National institute of standards and technology (NIST) 2006 mass spectral library. Identification was further confirmed by calculating the volatiles linear retention indices (RIs) using a series of n-alkanes (C5-C20) and comparing their values to published RI databases, namely that of Adams [Adams, R. P., Identification of essential oils by capillary gas chromatography/mass spectroscopy. Allured Publishing Corporation: Carol Stream, Ill., 2001] or Flavornet database (http://www.flavornet.org/flavornet.html). Major peaks were confirmed using authentic external standards, and peaks of interest were quantified by comparison with added toluene as the internal standard equivalents [Tietel, Z. et al., J. Sci. Food Agric. (2010), 90(6):995-1007].

Determination of Ethylene Content

During storage (12° C. for 22 days), an air sample (head space) was taken every few days. A 10 ml syringe was inserted through a silicone septum into each container. Ethylene concentration was determined using gas chromatography (Varian 3300) equipped with a flame ionization detector (GC-FID) and a HaySepR column (Hach Carle, Loveland, Colo., USA). Injection temperature was 100° C., column temperature was 100° C. and detector temperature was 155° C. The carrier gas (helium) flow rate was 30 mL/min. Ethylene concentration was calculated in relation to a known 1 L/L standard. The protocol was performed according to Pesis et al., [Pesis E. et al., (2000) Postharvest Biol. and Technol. 19:93-101].

Determination of Free SH Groups

Determination of free SH groups was performed according to the Ellman method [Ellman G. L. (1959) ibid.]. From each cultivar juice, 2 mL were added to an Eppendorf tube and stored at −18° C. On the day of analysis, the juice was thawed and spun at 12,000 RPM for 15 minutes. The clarified fluid was collected. To 0.5 mL clarified fluid, 1 mL phosphate buffer (pH 8) was added. The reaction was initiated by adding 50 L DTNB 2 mM, and spectrophotometric absorption was analyzed after 5 minutes in UltroSpec 2100pro at 412 nm [Ellman G. L. (1959) ibid.; Tapp E. J. et al., (2008) ibid.]. A control sample without DTNB was read and served as background. Absorption values were converted to SH groups concentration using an L cysteine calibration curve.

Determination of Total Soluble Solids (TSS)

Determination of TSS was performed on harvest day, after storage in refrigeration (12° C. for 22 days) and after shelf life (20° C. for 5 days). TSS was determined using a digital refractometer (Abbe model 10450) and provides an index for the juice sugar concentration. Juice acid content was determined by NaOH 0.1 M automated titration to pH 8.2 (TIM 850). Acidity was calculated according to citric acid, which is the predominant acid in *Passiflora* [Chan H. T. et al., (1972) J. Agric. Food Chem. 20:110-112]

Cell Line

Mouse hippocampal HT4 cells generated and provided by D. E. Koshland, Jr., University of California at Berkeley, were grown in Dulbecco's Modified Eagles Medium (DMEM) supplemented with 10% fetal calf serum, 1% glutamine, penicillin (100 U/ml), and streptomycin (100 mg/ml) at 37° C. in a humidified atmosphere containing 95% air and 5% $CO_2$.

Glucose Oxidase Challenge

The cells were washed with phosphate buffered saline (PBS) and detached with trypsin×2. Then cells were seeded in 6 well plates at the concentration of 30,000 cells/ml, 3 ml per well. The cells were left for overnight attachment and then were exposed to glucose oxidase 0.005 Um/l and to concentrate of different passion fruit cultivars while control cells were treated with PBS for 6 hours.

Cell Viability Evaluation after Glucose Oxidase Treatment

Cells were exposed to glucose oxidase 0.005 U/ml and to 0.3 ml concentrate of different passion fruit cultivars PD 100, 109, 230, 403, 428 and 440. Positive control cells were treated with glucose oxidase 0.005 U/ml and with NAC 20 mM. 6 hours later cells were harvested for cell viability evaluation using propidium iodide (PI) 2 µg/ml and flow cytometry (FACScalibur). Data were collected from 5,000 cells.

Glutamate Challenge

Semi-confluent cells are trypsinized and seeded on a culture dish or six-well plates at a concentration of 25,000 cells per ml. Following 24 h of seeding, the culture medium is replaced with fresh medium supplemented with serum and antibiotics as stated above, and the cells will are exposed to 10 mM glutamate according to a model of glutamate-induced cytotoxicity [Aharoni-Simon M et al., (2006) Antioxid Redox. Signal. 8:1339-1349].

Cell Viability Evaluation after Glutamate Treatment

Loss of cell-membrane integrity will be detected using PI staining. After 12 h glutamate treatment, cells are trypsinized, centrifuged (2,500 rpm, 5 min) and resuspended in PBS. Cells are filtered through a 90-µm Mesh grid, stained with PI (2 µg/ml) and evaluated by flow cytometry (FACScalibur) with the fluorescence setting: excitation at 488 nm and emission at 575 nm. Data were collected from 10,000 cells or 5,000 cells.

Evaluation of Dose Dependent/Boiled Passion Fruit Concentrate Protection

Cells exposed to glucose oxidase 0.005 U/ml were treated with indicated volumes of concentrate from PD or the new passion fruit cultivars. 6 hours later cells were harvested for cell viability evaluation using PI 2 mg/ml and flow cytometry (FACScalibur). Data were collected from 5,000 cells.

ROS Production Evaluation $H_2DCF$-reacting ROS (mainly peroxides) are detected by flow cytometer. Following the different treatments, cells are trypsinized, centrifuged (2,500 rpm, 5 min) and resuspended in PBS. Then the cells are filtered through a 90-mm mesh grid and incubated with $H_2DCF$ (25 µM) for 30 min at 37° C. The fluorescence is measured with excitation at 488 nm and emission at 530 nm. Superoxide levels are detected by dihydroethidium (DHE), dissolved to an initial concentration of 10 mM in dimethyl sulfoxide (DMSO). After the different treatments, the cells are incubated with 25 µM DHE in 1 ml PBS for 30 min at 37° C. The wells are washed three times with cold PBS; the cells are trypsinized and analyzed by flow cytometry with excitation at 488 nm and emission at 575 nm. Data is collected from 10,000 cells [Aharoni-Simon M et al., (2006) Antioxid Redox Signal 8:1339-1349].

Intracellular Glutathione (GSH) Assay

All cells are lysed with 1% orthophosphoric acid followed by snap-freezing and thawing, then centrifuged for 5 min at 10,000 g and the supernatant is collected. Standards and the supernatant are sealed in vials and automatically loaded (25 µl) into an HPLC-EC system. GSH and GSSG concentrations are measured by HPLC with online electrochemical detection. Stationary phase: reverse-phase Phenomenex Synergi column (250 mm×4.6 mm×4 µm). Mobile phase: 2% (v/v) acetonitrile in 50 mM $KH_2PO_4$ pH 2.7. GSH and GSSG are detected with an ESA Coulochem II electrochemical coulometric detector with a 5011 analytical cell run in oxidative mode (+850 mV). The flow rate for elution are maintained at 0.5 ml/min by an ESA pump [Budick-Harmelin N. et al., (2008), Antioxid. Redox. Signal. 10:2009-2022; Tirosh O. et al., (2003), Exp. Gerontol. 38:955-963].

Statistical Analysis

All values were expressed as means±SD (n=3 for each group). For multiple groups, differences were considered significant at probability levels of $P<0.05$ using the Tukey- Kramer HSD method. Statistical analysis was performed using the statistical computer program, JUMP version 7 (SAS Institute, Cary, N.C., USA).

Animals and Diets

Two-month-old male C57Bl/6 mice weighing 21-23 g are fed the appropriate diets for three months (N=12 mice/group). All diets contain 1% (1 g/kg diet) succinyl sulfathiozole, a non-absorbed sulfa drug, to control folate intake through caprophagy [Troen A. M. et al., (2008) J. Nutr. 138:2502-2509]. *Passiflora* are supplemented in the relevant diet in the form of a lyophilized extracts at a concentration of 1% (1 g/kg diet) after Joseph et al, 1998 [Joseph J. A. et al., (1998) J. Neurosci. 18:8047-8055]. Alternatively extracts are incorporated in the drinking water of the animals. Mice are fed water and diet ad libitum. Diet consumption is monitored to ensure comparable dietary and caloric intake. In the event of widely divergent food consumption by the different groups, pair feeding are implemented to ensure equivalent dietary intakes. After consuming the diet for 3 months (5-months-old at the time of MPTP administration), the mice are given a subtoxic dose of MPTP that does not result in detectable pathology or symptoms (two i.p. injections of 20 mg MPTP/kg body weight, separated by 4 h).

Neurochemical and Neuropathological Evaluation

After behavioral evaluation is complete, the mice are anesthetized with isoflurane and blood collected from the orbital sinus or submandibular vein. Plasma is separated frozen and stored at −80'C for subsequent folate and homocysteine determinations. Anesthetized mice will then be killed by cervical dislocation followed by decerebration. Brains are quickly removed and hemisected. Striatum, cortex, cerebellum and hippocampus are dissected from one hemisphere and the tissue snap frozen in liquid nitrogen. Levels of lipid peroxidation, GSH, folate and biogenic amine content are determined to allow the evaluation of the protective effect of the fruit. The other hemisphere is post-fixed in 4% buffered formalin solution for 48 h, then transferred to 30% sucrose in 0.1 M PB for at least 16 h until it sank for cryoprotection. The fixed tissues are embedded in OCT compound (polyvinyl glycol, polyvinyl alcohol, and water) and are frozen at −20° C. Coronal sections of 5 µm thicknesses will be cut on a Cryostat and transferred to gelatin-coated slides and immersed in wash buffer (sodium phosphate 100 mM, sodium chloride 0.5 M, triton X-100, sodium azide) pH 7.4 for 20 min. Thereafter, the slides are washed with PBS, and these sections are stained for dopaminergic neurons visualization with anti-tyrosine hydroxylase (TH) antibody. TH positive neurons in striatum and substantia nigra are evaluated qualitatively and quantitatively by using standard sampling techniques with NIH image J software.

Example 1

Physico-Chemical Characterization of the New Cultivar 428

Figure 1B:
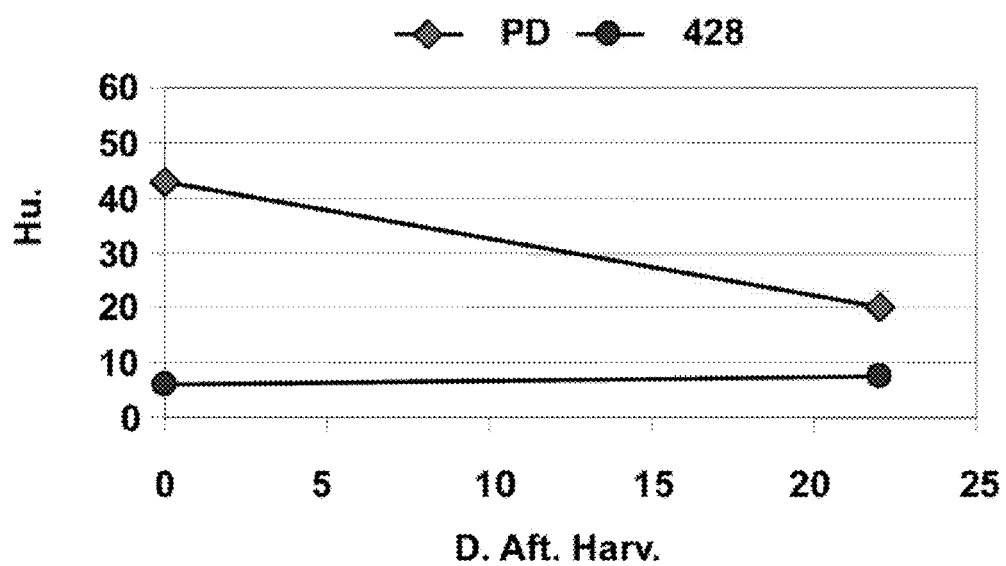
FIG. 1B: Fruit of 428 have a dark purple color in both winter and summer, and are darker in color compared to PD.
Figure 1C:
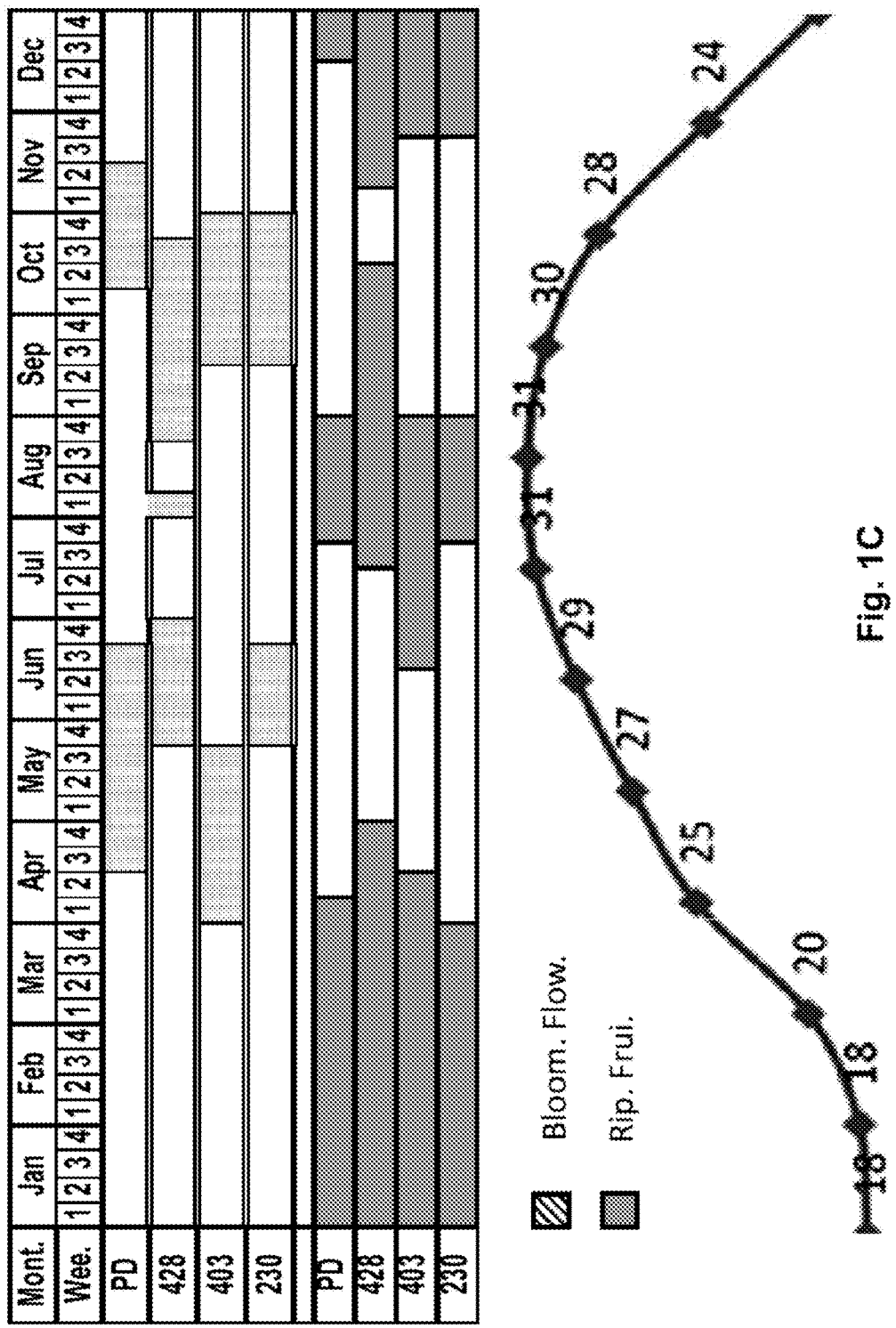
FIG. 1C: Blooming and ripe fruit seasons of different cultivars between April 2009 and March 2010 in the field in Rehovot, Israel. The dates are denoted from January for easier reading. Average daytime temperature is shown below.

Upon the identification of a new passion fruit cultivar, which the inventors designated as cultivar 428 (also referred to cultivar "RS" or "Dena"), they set about its characterization. FIG. 1A show the different morphology and skin color of the 428 cultivar fruit as compared to the known PD fruit. As can be seen, the 428 fruit is rounder and smaller than the PD fruit. 428 plants show much less vegetative growth compared to the PD cultivar, and in some conditions, 428 plants appear less green and more yellow, suggesting less chlorophyll due to lack of minerals such as iron. The skin hue of the 428 cultivar fruit is dark and purple, and remains so throughout summer and winter, while the skin of the PD fruit is lighter and changes gradually between seasons (FIG. 1B). FIG. 1C illustrates the blooming and ripe fruit seasons of different cultivars between April 2009 and March 2010 in Israel. Very similar blooming and fruit ripening seasons have been obtained in previous years. The blooming season of PD in the spring leads to fruit in the summer, and the blooming season starting the second week of October leads to ripe fruit during winter (starting mid-December). The cultivar 428 is unique in its flowering behavior, being capable of blooming during the warm summer (late June and also in the beginning of August). This summer bloom produces ripe fruit in September and beginning of October when other cultivars do not develop ripe fruit under the conditions examined.

Figure 1D:
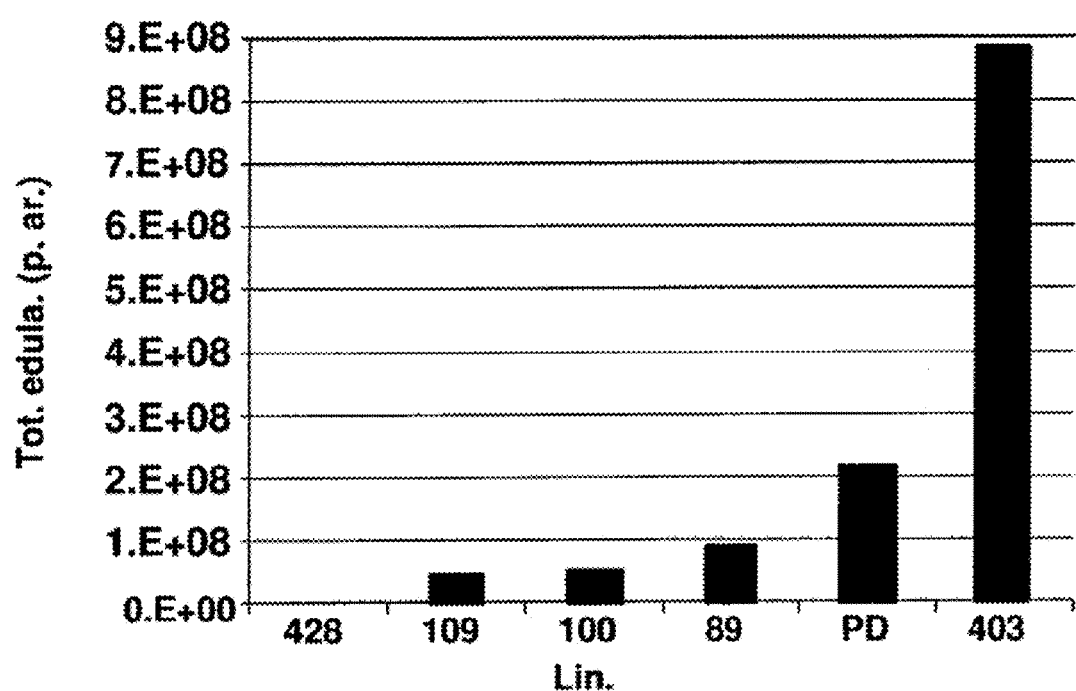
FIG. 1D: Amount of Edulan found in cultivars 428, 109, 100, 89, 403 and the parent PD.

Edulans (edulan I, $C_{13}H_{20}O$; edulan II, $C_{13}H_{20}O$), which have intense pleasant and unique note and are found in the volatile components of purple skinned *Passiflora edulis*. An analysis of edulans content in various cultivars revealed that the 428 cultivar produce negligible levels of them, whereas other cultivars produce edulans, as seen in FIG. 1D. Furthermore, seedlings from five self-crosses of 428 also produce very low levels of edulans.

Figure 1E:
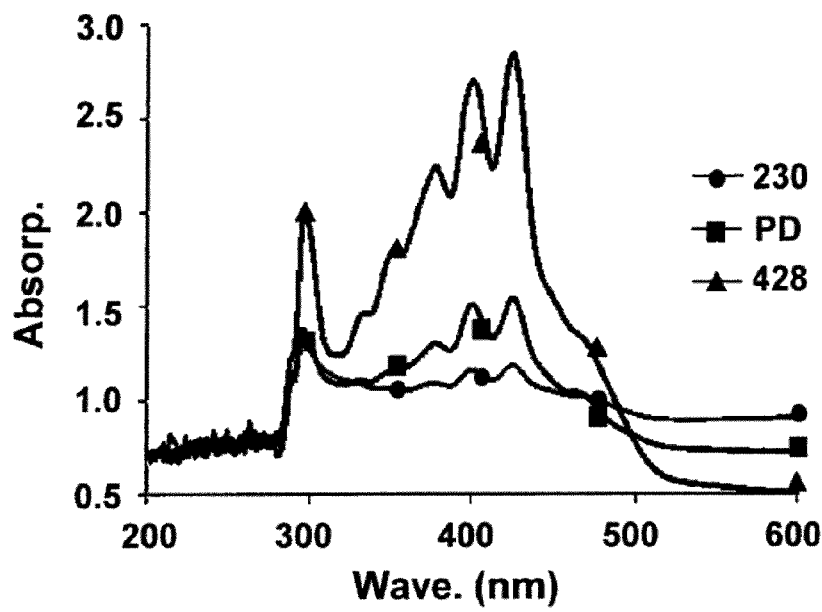
FIG. 1E: Spectra of carotenoids extracts of 230, PD and 428 cultivars fruit juice.

A spectrometric analysis of carotenoid content in three cultivars, PD, 428 and 230, illustrated in FIG. 1E, shows that the 428 cultivar contains a much higher carotenoid content compared to the other strains.

Figure 1F:
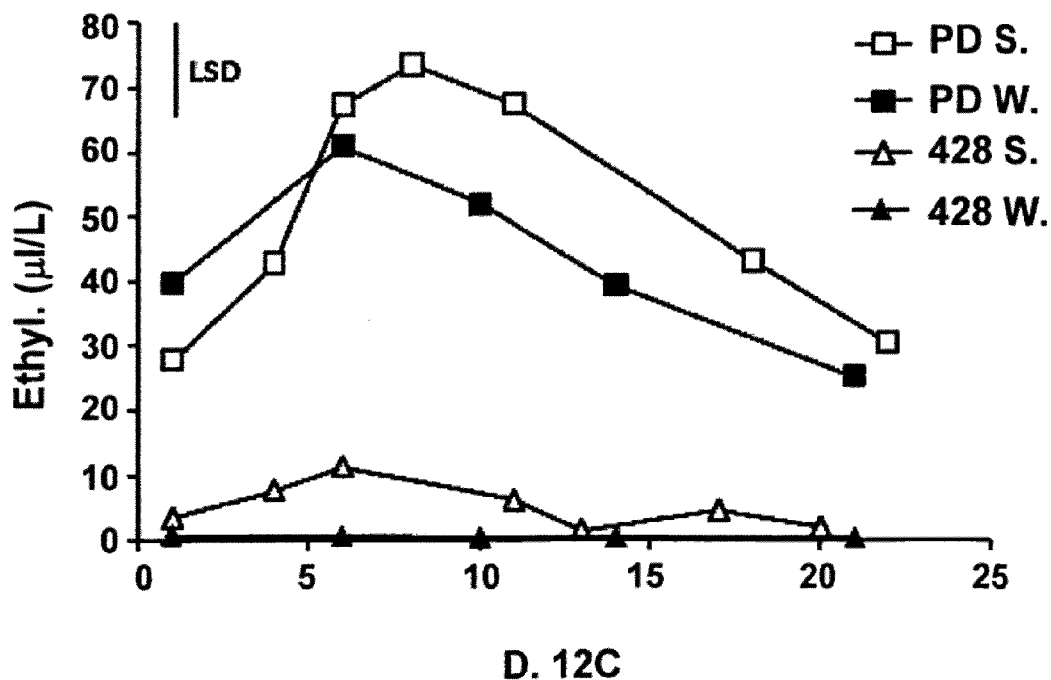
FIG. 1F: Levels of ethylene (ppm) in cultivars 428 and PD in winter and summer.

In passion fruit, high levels of ethylene production normally precede fruit abscission. Fruit that is collected from the ground normally already produces high levels of ethylene (70-230 ppm). During storage, the fruit still produces ethylene at a lower amount. The 428 cultivar is unique, since it does not seem to produce ethylene in the winter fruit, and that is likely the reason for the fruit not abscising. In the 2009-2010 winter, which was untypically warm, some of the winter fruit did not abscise and produced 3.5 ppm ethylene, compared to 1 ppm to fruits which were picked from the tree. In late summer, the 428 fruits which did abscise produced only low levels (1 ppm) of ethylene, as seen in FIG. 1F.

The inventors noted that the 428 fruit picked from the vine in winter is sour relative to all other varieties and is considered the least tasty. In summer, the 428 fruit which does abscise produces low levels of ethylene, is less sour and is tastier. An analysis of acidity and total soluble solids in PD, 428 and 440 cultivars, is shown in FIG. 1G and Table 1 below. The main reason for the difference in taste between winter and summer fruit of 428 is likely the higher acidity as measured by pH and % acid. It seems that reaching a pH of 3.9 and total soluble solids (TSS) levels of 16% are sufficient to achieve a tasty fruit (assuming volatiles contributing aroma are present).

TABLE 1

Acidity and total soluble solids content in PD (Passion Dream), 428 and 440 *Passiflora* cultivars during harvest and after storage.

| | | | pH | Acid (%) | TSS | TSS/Acid ratio |
|---|---|---|---|---|---|---|
| PD | Feb-09 | Harvest | 3.89 | 1.26 | 17.40 | 13.81 |
| | | After storage | 4.40 | 0.72 | 15.80 | 21.94 |
| 428 | Feb-09 | Harvest | 3.49 | 1.73 | 16.50 | 9.54 |
| | | After storage | 3.40 | 2.36 | 13.30 | 5.64 |
| | Sep-09 | Harvest | 3.94 | 1.07 | 17.63 | 16.75 |
| | | After storage | 3.95 | 1.38 | 16.67 | 12.26 |

TABLE 1-continued

Acidity and total soluble solids content in PD (Passion Dream), 428 and 440 *Passiflora* cultivars during harvest and after storage.

|     |        |               | pH   | Acid (%) | TSS   | TSS/Acid ratio |
|-----|--------|---------------|------|----------|-------|----------------|
| 440 | Sep-09 | Harvest       | 3.64 | 1.75     | 16.20 | 9.25           |
|     |        | After storage | 3.82 | 1.49     | 13.97 | 9.39           |

Another interesting feature of the 428 cultivar is its low amount of total volatiles and esters as compared to the PD cultivar, especially during the winter, shown in FIG. 2A. This was further echoed in the GC-MS analysis of volatiles in summer (FIG. 2B) and winter (FIG. 2C) 428 fruit, which demonstrate this large difference. The GC-MS-detected volatiles values, normalized to concentration (μl/L), is provided in Table 2 below. The seasons difference ratio (SDR) provided in the table allows a convenient view on the major changes the 428 and PD cultivars undergo in terms of volatiles content during seasonal changes, and emphasizes volatiles that change dramatically different in the two cultivars (e.g., methyl butanoate, ethyl butanoate, methyl hexanoate and ethyl).

TABLE 2

Winter and summer volatiles concentrations in the *Passiflora* cultivars 428 and PD (Passion Dream) on harvest day.

| Compound | RI$^a$ | RI$^b$ | Concentration (μl/L) Line PD Summer | Winter | 428 Summer | Winter | SDR$^f$ PD | 428 |
|---|---|---|---|---|---|---|---|---|
| ethyl acetate | 651 | 628$^c$ | 1.07$^a$ | 0.21$^a$ | 0.57$^a$ | 0.07$^a$ | 5.33 | 8.51 |
| methyl butanoate | 754 | 729 | 0.06$^a$ | 0.04$^a$ | 0.06$^a$ | 0.0001$^a$ | 2.05 | 628.08 |
| ethyl butanoate | 812 | 804 | 11.04$^a$ | 5.64$^{ab}$ | 7.97a | 0.19$^b$ | 2.47 | 41.57 |
| butyl acetate | 825 | 811 | 0.63$^a$ | 0.25$^{ab}$ | 0.23$^{ab}$ | 0.03$^b$ | 2.94 | 8.76 |
| hexanol | 879 | 854 | 0.40$^a$ | 0.19$^b$ | 0.47$^a$ | 0.06$^b$ | 2.62 | 8.07 |
| 2-heptanone | 901 | 892 | 0.74$^a$ | 0.11$^b$ | 0.10$^b$ | 0.0010$^b$ | 7.16 | 101.44 |
| methyl hexanoate | 936 | 927 | 0.03$^a$ | 0.02$^a$ | 0.15$^a$ | 0.0001$^a$ | 2.12 | 1538.90 |
| heptanol | 981 | 967 | 0.03$^a$ | 0.01$^a$ | 0.02$^a$ | 0.01$^a$ | 2.41 | 2.82 |
| 6-methyl 5-hepten 2-one | 999 | 986 | 0.17$^b$ | 0.49$^a$ | 0.02$^c$ | 0.04$^c$ | 3.17 | 2.33 |
| β myrcene | 1003 | 991 | 0.44$^a$ | 0.50$^a$ | 0.39$^a$ | 0.06$^a$ | 2.01 | 6.54 |
| butyl butanoate | 1007 | 995 | 1.49$^a$ | 0.86$^a$ | 0.22$^a$ | 0.01$^a$ | 2.31 | 31.37 |
| ethyl hexanoate | 1011 | 998 | 9.00$^a$ | 4.58$^a$ | 12.55$^a$ | 0.13$^a$ | 2.47 | 93.49 |
| 3 hexenyl acetate | 1019 | 1005 | 1.18$^a$ | 1.07$^a$ | 1.25$^a$ | 0.14$^b$ | 2.01 | 8.97 |
| hexyl acetate | 1025 | 1009 | 1.85$^{ab}$ | 1.26$^{ab}$ | 2.84$^a$ | 0.24$^b$ | 2.15 | 11.89 |
| limonene | 1044 | 1029 | 0.27$^a$ | 0.18$^a$ | 0.28$^a$ | 0.05$^a$ | 2.16 | 5.45 |
| methylhexyl acetate | 1054 | 1044 | 0.75$^a$ | 0.02$^b$ | 0.64$^{ab}$ | 0.01$^b$ | 30.24 | 111.29 |
| cis-β-ocimene | 1062 | 1050 | 2.30$^a$ | 0.39$^b$ | 0.32$^b$ | 0.02$^b$ | 5.99 | 13.49 |
| octanol | 1083 | 1068 | 0.22$^{ab}$ | 0.08$^b$ | 0.45$^a$ | 0.03$^b$ | 2.96 | 16.03 |
| linalool | 1114 | 1097 | 0.76$^a$ | 0.51$^{ab}$ | 0.18$^{ab}$ | 0.08$^b$ | 2.17 | 2.66 |
| hexyl propanoate | 1121 | 1108$^d$ | 0.15$^a$ | 0.21$^a$ | 0.09$^a$ | 0.04$^a$ | 2.12 | 2.64 |
| rose oxide | 1127 | 1108 | 0.18$^a$ | 0.03$^b$ | 0.02$^b$ | 0.0001b | 5.52 | 167.36 |
| ethyl 3hydroxy hexanoate | 1142 | 1133$^d$ | 0.01$^a$ | 0.03$^a$ | 0.05$^a$ | 0.0001$^a$ | 4.99 | 548.02 |
| benzyl acetate | 1182 | 1162 | 0.20$^a$ | 0.13$^{ab}$ | 0.25$^a$ | 0.02$^b$ | 2.18 | 13.18 |
| 3 hexenyl butyrate | 1202 | 1186 | 5.27$^a$ | 3.94$^a$ | 2.30$^a$ | 0.30$^a$ | 2.09 | 7.71 |
| hexyl butanoate | 1211 | 1193 | 30.03$^a$ | 19.31$^{ab}$ | 19.99$^{ab}$ | 1.51$^b$ | 2.20 | 13.31 |
| methylhexyl butanoate | 1231 | 1194$^e$ | 13.25$^a$ | 1.67$^{bc}$ | 7.33$^{ab}$ | 0.04$^c$ | 8.04 | 185.42 |
| hexyl 2-methyl butanoate | 1253 | 1236 | 0.24$^b$ | 0.11$^b$ | 0.69$^a$ | 0.11$^b$ | 2.69 | 6.59 |
| 3-mercaptohexyl acetate | 1269 | 1244$^c$ | 0.01$^b$ | 0.01$^b$ | 0.06$^a$ | 0.004$^b$ | 2.02 | 14.19 |

TABLE 2-continued

Winter and summer volatiles concentrations in the *Passiflora* cultivars 428 and PD (Passion Dream) on harvest day.

| | | | Concentration (μl/L) Line | | | | | |
|---|---|---|---|---|---|---|---|---|
| | | | PD | | 428 | | SDR[f] | |
| Compound | RI[a] | RI[b] | Summer | Winter | Summer | Winter | PD | 428 |
| geraniol | 1287 | 1253 | 0.16[a] | 0.08[a] | 0.09[a] | 0.01[a] | 2.51 | 11.35 |
| dihydro edulan I | 1325 | 1292[e] | 0.85[a] | 0.04[ab] | 0.12[b] | 0.004[ab] | 22.25 | 29.21 |
| edulan I | 1343 | 1309 | 2.14[a] | 0.76[ab] | 0.53[b] | 0.02[ab] | 3.18 | 34.86 |
| benzyl butanoate | 1370 | 1347 | 0.48[a] | 0.14[ab] | 0.25[b] | 0.02[ab] | 3.67 | 15.39 |
| TDN* | 1387 | 1354[e] | 0.81[a] | 0.0001[c] | 0.34[b] | 0.01[c] | 8124.99 | 45.39 |
| 3 hexenyl hexanoate | 1402 | 1381[c] | 3.80[a] | 3.30[a] | 3.12[a] | 0.45[a] | 2.02 | 7.05 |
| hexyl hexanoate | 1409 | 1384 | 20.67[a] | 17.1[ab] | 22.18[a] | 2.29[b] | 2.04 | 9.78 |
| methylhexyl hexanoate | 1424 | 1390[e] | 8.79[a] | 1.45[b] | 8.01[a] | 0.08[b] | 6.21 | 100.06 |
| geranyl acetone | 1478 | 1455 | 0.52[ab] | 0.97[a] | 0.33[ab] | 0.04[b] | 2.41 | 7.45 |
| β ionone | 1522 | 1489 | 0.27[a] | 0.08[b] | 0.07[b] | 0.02[b] | 3.84 | 3.55 |

[a]Calculated retention indices (RI) using a series of n-alkanes;
[b]Published retention indices on DB-5 column according to Adams [Adams, R. P., Identification of essential oils by capillary gas chromatography/mass spectroscopy. Allured Publishing Corporation: Carol Stream, IL, 2001], or:
[c]Flavornet Database (http://www.flavornet.org/flavornet.html);
[d]ISCA Technologies Database (http://www.pherobase.com/database/kovats/kovats-index.php);
[e][Pino, J. A.; et al., (2002) J. Agri. Food Chem., 50: 5146-5148; Campeol, E.; et al. (2001); J. Agri. Food Chem. 49: 5409-5411; Demyttenaere, J. C. R.; et al. J. Chromatogr. A (2003) 985: 233-246];
[f]Values followed by the same letter within a row are not significantly different at P = 0.05 (Tukay test); [g]SDR—Seasons difference ratio.

Example 2

Passion Fruit Cultivars PD (Passion Dream) and 428 Extracts Protects HT-4 Cells from Glucose Oxidase Challenge HT-4 cell line treated with glucose oxidase demonstrated extensive death as a result of oxidative stress induced by this enzyme. Concomitant treatment with glucose oxidase and a concentrate of different passion fruit cultivars harvested on several dates revealed that all cultivars examined are able to protect from cell death induced by the glucose oxidase treatment. This protection against cell death was shown to be more effective in cells treated with passion fruit concentrate than in the positive control cells treated with NAC, as can be clearly seen in FIGS. 3A-3C. The highest percentage of cell viability was observed after treatment with extracts from cultivar 428 and PD, as shown in FIGS. 3B and 3C.

Example 3

The Component from Passion Fruit Cultivars PD (Passion Dream) and 428 Extracts which Protects HT-4 Cells from Glucose Oxidase Challenge Acts in a Dose-Dependent Manner and is Heat-Labile FIGS. 4A and 4B show that treatment with the concentrate of these two cultivars after induction of cell death by glucose oxidase as in Example 1 revealed that the protective effect is dose dependent and therefore may increase with higher doses of concentrate. Boiling the concentrate reduced its positive effect significantly (FIG. 4C).

Example 4

Passion Fruit Cultivar 428 Extracts, but not PD (Passion Dream) Extracts, Protects HT-4 Cells from Glutamate Challenge Cultivar 428 concentrate also protected HT-4 cells from glutamate induced cell death after 24 hours of treatment. In contrast, FIG. 5A shows that the PD cultivar concentrate did not achieve any similar protection results in cells exposed to glutamate.

Flow cytometric analysis of DCF fluorescence in cells treated with 428 or PD cultivar concentrate for 6 hours indicated that treatment with these cultivars extracts reduced reactive oxygen species (ROS) levels in the cells. FIG. 5B demonstrates that treatment with the cultivar 428 extracts reduces cellular ROS levels significantly more than the PD cultivar extract.

Example 5

Improvement of the Neuroprotective Properties of the 428 Cultivar

The data shows that extracts of line 428 possess potent neuroprotective activity in cell culture. These extracts of fruit juice were shown by the invention more potent than NAC, which is a well-established neuroprotective compound that has been clinically tested in humans and is marketed as a nutraceutical. The inventors study the next generation of selfed 428 lines and test their ability to provide higher levels of protection. In addition, extracts from different lines are mixed and tested for possible synergistic activity. Identifying synergistic activity in combined extracts allows the inventors to breed and select lines that combine the traits of each of the mixture lines within one superior cultivar.

Example 6

In Vivo Assessment of the Neuroprotective Effects of Passion Fruit Cultivar 428 Extracts The inventors determine the neuroprotective effect of selected lines in vivo using behavioral, neurochemical and neuropathological outcomes, in a well established model of chemically induced Parkinson's disease, using those lines selected for optimal in vitro activity.

The neuroprotective effects exerted by *Passiflora* are assessed in vivo in the mouse MTPT (1-methyl-4-phenyl-1,2,3,6-tetrahydropyridine) model, as described in the Experimental Procedures section above. Exposure to MPTP induces severe oxidative stress following impairment of mitochondrial respiration by the inhibition of complex I of the electron transport chain. Striatal dopaminergic neurons are particularly sensitive to this insult, and their subsequent degeneration partially recapitulates the behavioral and neuropathological features of Parkinson's disease.

Mice are administered MPTP i.p. (two i.p. injections of 20 mg MPTP/kg body eight, separated by 4 h) following a normal or a folate-deficient diet, supplemented with *Passiflora* extract or not. Resulting psychomotor deficits are readily measured using the accelerating rotarod test. Mice sensitized with a folate deficient diet develop significant psychomotor deficits due to production of ROS and consequent loss of 50-60% of tyrosine hydroxylase positive dopaminergic neurons in the substantia nigra. It is expected that administration of *Passiflora* extract protects folate deficient mice from MPTP-induced damage to dopaminergic neurons. The extent of protection is quantitatively expressed as the percent neuronal loss and behavioral impairment relative to the folate deficient (positive control) and folate replete (negative control) groups.

Behavioral Evaluation

Mice are assessed behaviorally 1 day prior to, and 7 days after, MPTP administration. The primary behavioral outcome is psychomotor performance on the rotary rod apparatus [Shukitt-Hale B et al., (1998), Exp. Gerontol. 33:615-624; Troen A. M. et al., (2006) J. Alzheimer's. Dis. 9:381-392]. Mice are placed on a gradually accelerating rotating rod and the time until they fall off is automatically recorded. This is be repeated (with a rest period increasing by 5 s with each fall) until the total time on the rod is 5 min. Both the total time spent on the rotating rod and the total number of falls for each mouse are recorded.

Neurochemical and Neuropathological Evaluation

After behavioral evaluation is complete, the mice blood folate and homocysteine levels are determined as described in the Experimental Procedures section above. Levels of lipid peroxidation, GSH, folate and biogenic amine content are determined for the striatum, cortex, cerebellum and hippocampus, to allow the evaluation of the protective effect of the fruit, fixed brain tissues are stained for dopaminergic neurons visualization. Tyrosine hydroxylase (TH) positive neurons in striatum and substantia nigra are evaluated qualitatively and quantitatively.

What is claimed is:

1. A method for protecting neural cells in a subject having age-related neurodegeneration, said method comprising the step of administering to said subject an effective amount of botanical raw material (BRM) or an extract obtained from passion fruits, wherein said BRM or an extract obtained from passion fruits is any one of a juice or seeds obtained from passion fruits, or any concentrate or preparation obtained from said juice or seeds.

2. The method according to claim 1, wherein said BRM or an extract obtained from passion fruits is any one of a juice or seeds obtained from at least one variety or cultivar of passion fruits or a mixture of two or more cultivars of passion fruits, or any concentrate or preparation obtained from said juice or seeds.

3. The method according to claim 1, wherein said BRM or an extract obtained from passion fruits is administered as part of a nutraceutical composition, pharmaceutical composition, functional food, functional nutrition product, medical food, medical nutrition product or dietary supplement.

4. A method for protecting from, inhibiting or reducing cognitive decline in a subject having age-related neurodegeneration, said method comprising the step of administering to said subject an effective amount of botanical raw material (BRM) or an extract obtained from passion fruits, wherein said BRM or an extract obtained from passion fruits is any one of a juice or seeds obtained from passion fruits, or any concentrate or preparation obtained from said juice or seeds.

5. The method according to claim 4, wherein said BRM or an extract obtained from passion fruits is any one of a juice or seeds obtained from at least one variety or cultivar of passion fruits or a mixture of two or more cultivars of passion fruits, or any concentrate or preparation obtained from said juice or seeds.

6. The method according to claim 4, wherein said BRM or an extract obtained from passion fruits is administered as part of a nutraceutical composition, pharmaceutical composition, functional food, functional nutrition product, medical food, medical nutrition product or dietary supplement.

7. A method for the treatment, amelioration or inhibition of age-related neurodegeneration in a subject having age-related neurodegeneration, said method comprising the step of administering to said subject an effective amount of BRM or an extract obtained from passion fruits, wherein said BRM or an extract obtained from passion fruits is any one of a juice or seeds obtained from passion fruits, or any concentrate or preparation obtained from said juice or seeds, wherein said subject has age-related neurodegeneration.

8. The method according to claim 7, wherein said BRM or an extract obtained from passion fruits is administered as part of a nutraceutical composition, pharmaceutical composition, functional food, functional nutrition product, medical food, medical nutrition product or dietary supplement.

* * * * *